(12) United States Patent
Takeda

(10) Patent No.: US 12,315,619 B2
(45) Date of Patent: May 27, 2025

(54) BLOOD SUGAR MANAGEMENT DEVICE, BLOOD SUGAR MANAGEMENT SYSTEM, BLOOD SUGAR MANAGEMENT METHOD, AND BLOOD SUGAR MANAGEMENT PROGRAM

(71) Applicant: TERUMO KABUSHIKI KAISHA, Tokyo (JP)

(72) Inventor: Mei Takeda, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 373 days.

(21) Appl. No.: 17/726,099

(22) Filed: Apr. 21, 2022

(65) Prior Publication Data
US 2022/0246278 A1 Aug. 4, 2022

Related U.S. Application Data

(63) Continuation of application No. PCT/JP2020/031554, filed on Aug. 21, 2020.

(30) Foreign Application Priority Data

Oct. 30, 2019 (JP) ................................ 2019-196828

(51) Int. Cl.
*G16H 20/60* (2018.01)
*A61B 5/00* (2006.01)
(Continued)

(52) U.S. Cl.
CPC ........... *G16H 20/60* (2018.01); *A61B 5/4866* (2013.01); *A61B 5/7282* (2013.01); *G16H 10/40* (2018.01); *A61B 5/14532* (2013.01)

(58) Field of Classification Search
CPC ...... G16H 20/60; G16H 10/40; A61B 5/4866; A61B 5/7282; A61B 5/14532
See application file for complete search history.

(56) References Cited

U.S. PATENT DOCUMENTS 7,215,983 B2 * 5/2007 Cho .................... A61B 5/14532
600/326
7,251,515 B2 * 7/2007 Cho ..................... A61B 5/7475
600/326
(Continued)

FOREIGN PATENT DOCUMENTS

CN 102028542 A 4/2011
JP 2011-117911 A 6/2011
(Continued)

OTHER PUBLICATIONS

Cholesterol metabolism, Morgan, Elsevier, 2016, pp. 108-124.*
(Continued)

*Primary Examiner* — Michael I Ezewoko
(74) *Attorney, Agent, or Firm* — Foley & Lardner LLP

(57) ABSTRACT

A blood sugar management device includes a blood sugar information acquisition unit, a meal information acquisition unit, a storage unit, a blood sugar determination unit, and an information organization unit. When the blood sugar determination unit determines that a measured blood sugar value is within a predetermined range, the information organization unit deletes meal information corresponding to the measured blood sugar value from the storage unit, and when the blood sugar determination unit determines that the measured blood sugar value is not within the predetermined range, the information organization unit holds meal information corresponding to the measured blood sugar value in the storage unit.

14 Claims, 13 Drawing Sheets

(51) Int. Cl.
*G16H 10/40* (2018.01)
*A61B 5/145* (2006.01)

(56) References Cited

U.S. PATENT DOCUMENTS

| | | | | |
|---|---|---|---|---|
| 7,254,426 B2* | 8/2007 | Cho | ............... | A61B 5/14532 600/326 |
| 7,376,591 B2* | 5/2008 | Owens | ............... | G06Q 30/0629 705/26.8 |
| 7,882,150 B2* | 2/2011 | Badyal | ............... | G06Q 10/10 707/803 |
| 8,015,076 B2* | 9/2011 | Owens | ............... | G06Q 30/0277 705/26.64 |
| 8,868,436 B2* | 10/2014 | Gotthardt | ............... | G16H 50/70 705/2 |
| 8,878,669 B2* | 11/2014 | Nothacker | ............... | A61B 5/7275 340/539.12 |
| 9,076,317 B2* | 7/2015 | Nothacker | ............... | G08B 21/02 |
| 9,192,334 B2* | 11/2015 | Nothacker | ............... | A61B 5/082 |
| 9,367,727 B2* | 6/2016 | Mochizuki | ............... | G06F 16/5838 |
| 9,384,505 B1* | 7/2016 | Cao | ............... | G06Q 30/0633 |
| 9,600,632 B2* | 3/2017 | Nothacker | ............... | A61B 5/743 |
| 9,662,065 B2* | 5/2017 | Nothacker | ............... | G16H 40/67 |
| 9,740,827 B2* | 8/2017 | Nothacker | ............... | G01N 33/4972 |
| 9,866,749 B2* | 1/2018 | Relf | ............... | H04N 1/00244 |
| 9,872,649 B2* | 1/2018 | Nothacker | ............... | G08B 21/02 |
| 9,974,486 B2* | 5/2018 | Nagasaki | ............... | A61B 5/7435 |
| 9,996,673 B2* | 6/2018 | Nothacker | ............... | A61B 5/097 |
| 10,013,755 B2* | 7/2018 | Mochizuki | ............... | G06F 16/5838 |
| 10,034,635 B2* | 7/2018 | Nothacker | ............... | A61B 5/097 |
| 10,497,040 B2* | 12/2019 | Cao | ............... | G06Q 30/0625 |
| 10,567,906 B1* | 2/2020 | Iqbal | ............... | G06F 16/1824 |
| 10,653,317 B2* | 5/2020 | Fennell | ............... | A61B 5/1473 |
| 10,653,344 B2* | 5/2020 | Hayter | ............... | G16H 20/10 |
| 10,653,358 B2* | 5/2020 | Nothacker | ............... | G16Z 99/00 |
| 10,656,139 B2* | 5/2020 | Ou | ............... | G01N 33/49 |
| 10,660,554 B2* | 5/2020 | Hayter | ............... | A61B 5/1495 |
| 10,736,548 B2* | 8/2020 | Ahmad | ............... | G16H 20/60 |
| 10,750,952 B2* | 8/2020 | Jin | ............... | A61B 5/14532 |
| 10,820,841 B2* | 11/2020 | Hayter | ............... | A61B 5/1495 |
| 10,872,102 B2* | 12/2020 | Wei | ............... | G16H 40/60 |
| 10,939,859 B2* | 3/2021 | Hayter | ............... | A61B 5/746 |
| 10,942,164 B2* | 3/2021 | Ou | ............... | G16Z 99/00 |
| 10,952,611 B2* | 3/2021 | Fennell | ............... | A61B 5/1468 |
| 10,976,304 B2* | 4/2021 | Hayter | ............... | G16H 10/40 |
| 10,991,456 B2* | 4/2021 | Hayter | ............... | A61B 5/4839 |
| 11,039,767 B2* | 6/2021 | Hayter | ............... | A61B 5/0033 |
| 11,045,147 B2* | 6/2021 | Fennell | ............... | A61B 5/7228 |
| 11,076,785 B2* | 8/2021 | Hayter | ............... | A61B 5/1473 |
| 11,083,843 B2* | 8/2021 | Hayter | ............... | A61B 5/14532 |
| 11,119,090 B2* | 9/2021 | Hayter | ............... | G16H 10/40 |
| 11,125,592 B2* | 9/2021 | Hayter | ............... | A61B 5/7221 |
| 11,132,730 B2* | 9/2021 | Cao | ............... | G06Q 20/14 |
| 11,150,145 B2* | 10/2021 | Nekoomaram | ............... | A61B 5/0002 |
| 11,159,911 B2* | 10/2021 | Iqbal | ............... | H04W 4/025 |
| 11,213,226 B2* | 1/2022 | Fennell | ............... | A61B 5/14865 |
| 11,234,625 B2* | 2/2022 | Hayter | ............... | A61B 5/4839 |
| 11,300,561 B2* | 4/2022 | Hayter | ............... | G16H 10/40 |
| 11,393,588 B2* | 7/2022 | Nothacker | ............... | G01N 33/98 |
| 11,646,120 B2* | 5/2023 | Nothacker | ............... | A61B 5/4863 340/576 |
| 2004/0225209 A1* | 11/2004 | Cho | ............... | A61B 5/14532 600/326 |
| 2005/0070777 A1* | 3/2005 | Cho | ............... | G01K 3/10 600/326 |
| 2007/0168228 A1* | 7/2007 | Lawless | ............... | G06Q 40/08 600/300 |
| 2011/0225114 A1* | 9/2011 | Gotthardt | ............... | G16H 10/20 706/50 |
| 2014/0119614 A1* | 5/2014 | Mochizuki | ............... | G06T 7/001 382/110 |
| 2014/0210627 A1* | 7/2014 | Nothacker | ............... | G01N 33/4972 340/576 |
| 2014/0243261 A1* | 8/2014 | Gilbert | ............... | A61K 38/28 514/23 |
| 2014/0257855 A1* | 9/2014 | Moore | ............... | G16H 40/67 705/2 |
| 2014/0335481 A1* | 11/2014 | Butler | ............... | G16H 20/60 434/127 |
| 2014/0361900 A1* | 12/2014 | Nothacker | ............... | A61B 5/0077 340/576 |
| 2015/0106726 A1* | 4/2015 | Nagasaki | ............... | G06F 3/04842 715/739 |
| 2015/0130830 A1* | 5/2015 | Nagasaki | ............... | G16H 20/60 345/592 |
| 2015/0154623 A1* | 6/2015 | Jin | ............... | G06Q 30/02 705/14.27 |
| 2015/0164416 A1* | 6/2015 | Nothacker | ............... | A61B 5/18 340/573.1 |
| 2015/0261927 A1* | 9/2015 | Nothacker | ............... | A61B 5/18 702/19 |
| 2015/0294064 A1* | 10/2015 | Bevilacqua | ............... | G01N 33/5088 702/19 |
| 2016/0045153 A1* | 2/2016 | Nothacker | ............... | A61B 5/4863 600/532 |
| 2016/0132642 A1* | 5/2016 | Carmi | ............... | H04N 5/144 348/77 |
| 2016/0284074 A1* | 9/2016 | Mochizuki | ............... | G06F 16/24 |
| 2017/0027504 A1* | 2/2017 | Nothacker | ............... | A61B 5/742 |
| 2017/0046493 A1* | 2/2017 | Nothacker | ............... | A61B 5/097 |
| 2017/0164889 A9* | 6/2017 | Nothacker | ............... | A61B 5/4845 |
| 2017/0181696 A1* | 6/2017 | Nothacker | ............... | G08B 21/0453 |
| 2018/0103881 A1 | 4/2018 | Choi et al. | | |
| 2018/0131870 A1* | 5/2018 | Relf | ............... | H04N 1/00156 |
| 2018/0289321 A1* | 10/2018 | Nothacker | ............... | A61B 5/4845 |
| 2018/0301225 A1* | 10/2018 | Nothacker | ............... | A61B 5/097 |
| 2019/0385209 A1* | 12/2019 | Cao | ............... | G06Q 20/14 |
| 2020/0169837 A1* | 5/2020 | Iqbal | ............... | H04W 4/021 |

FOREIGN PATENT DOCUMENTS

| | | | |
|---|---|---|---|
| JP | 2011-206486 A | 10/2011 | |
| JP | 2019-028625 A | 2/2019 | |
| KR | 20180090076 A | 8/2018 | |
| WO | WO-2014/162549 A1 | 10/2014 | |
| WO | WO-2019/098600 A1 | 5/2019 | |

OTHER PUBLICATIONS

Enabling Health Informatics Applications, Mantas, IOS Press, 2015, pp. 53-56.*

The Last Well Person, 2004, Hadler, Chapter 2.*

International Searching Authority, "Written Opinion," issued in connection with PCT Patent Application No. PCT/JP2020/031554, dated Oct. 13, 2020, with English Translation.

Extended European Search Report issued in connection with EP Appl. Ser. No. 20882027.4 dated Oct. 6, 2022.

International Searching Authority, "International Search Report," issued in connection with International Patent Application No. PCT/JP2020/031554, dated Oct. 13, 2020.

International Searching Authority, "Written Opinion," issued in connection with International Patent Application No. PCT/JP2020/031554, dated Oct. 13, 2020.

* cited by examiner

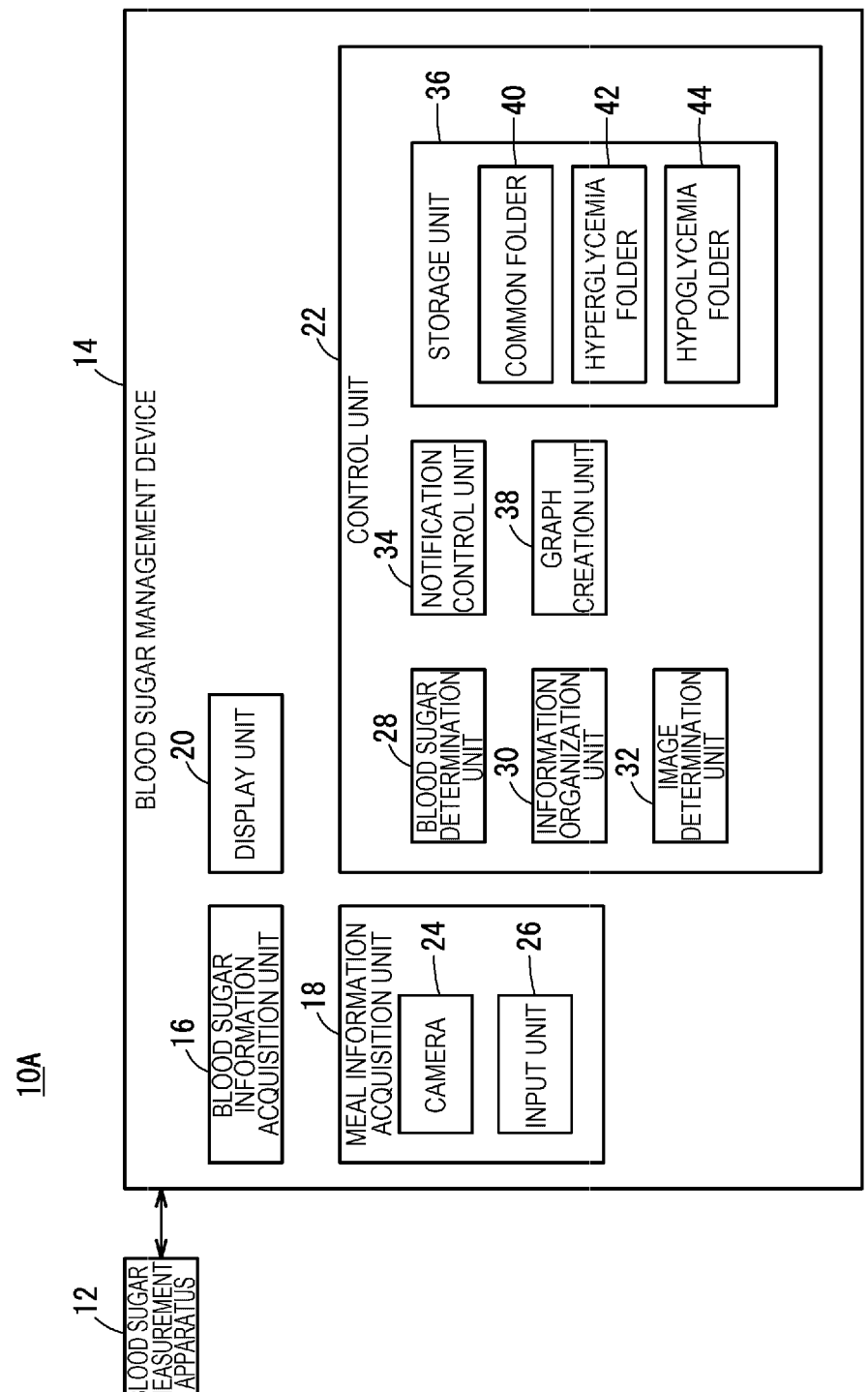
[FIG. 1]

[FIG. 2]
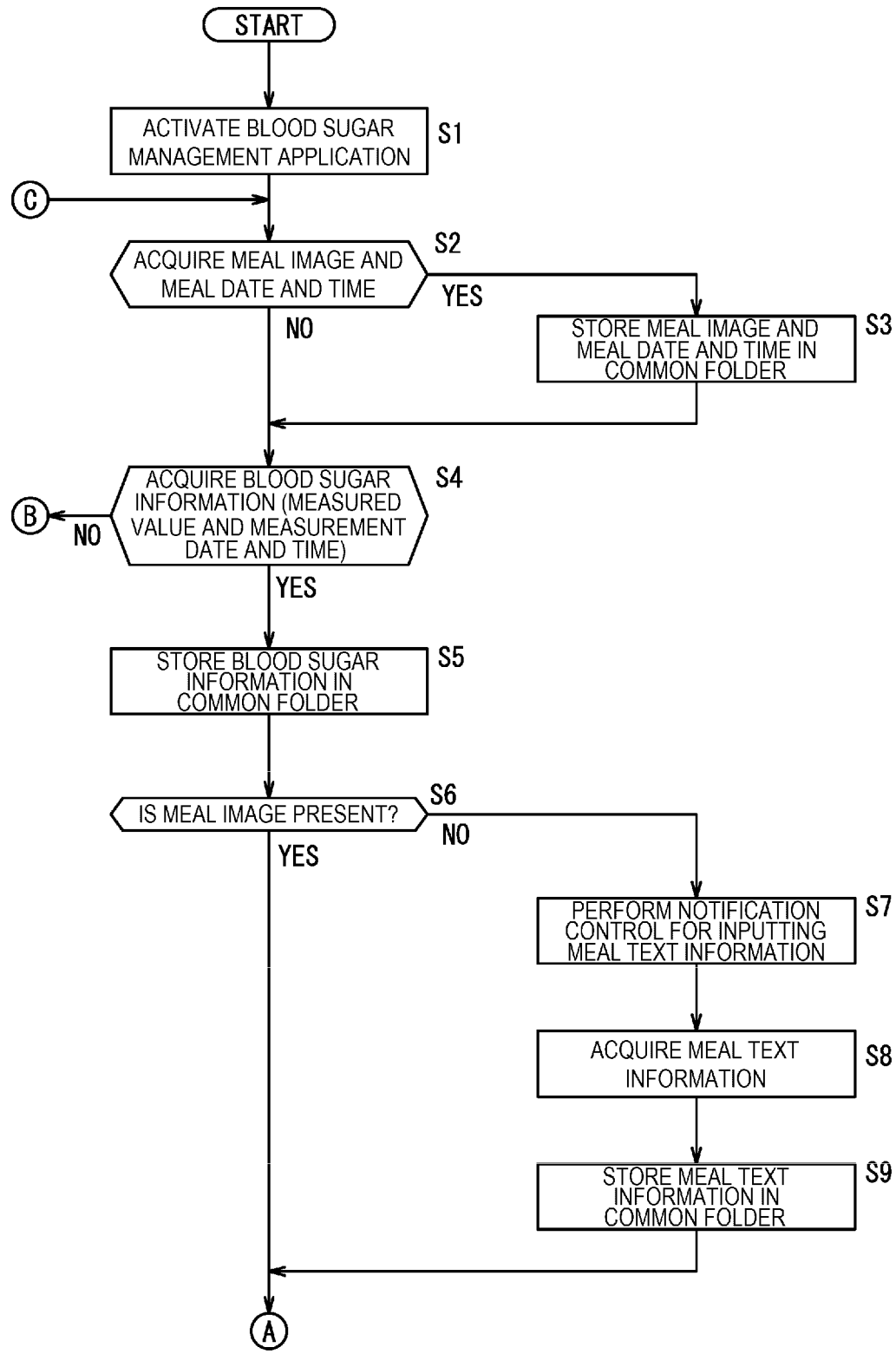

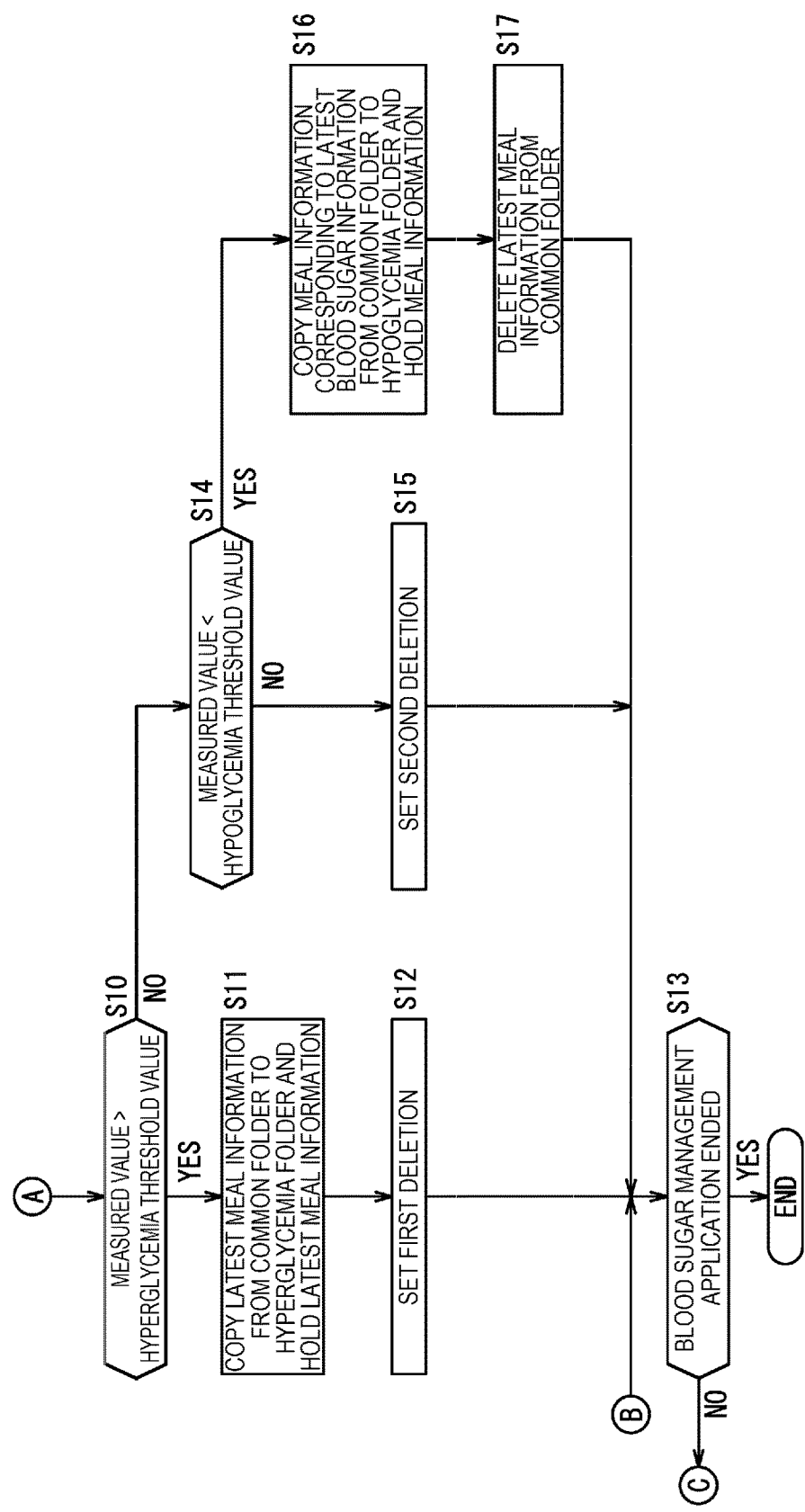
[FIG. 3]

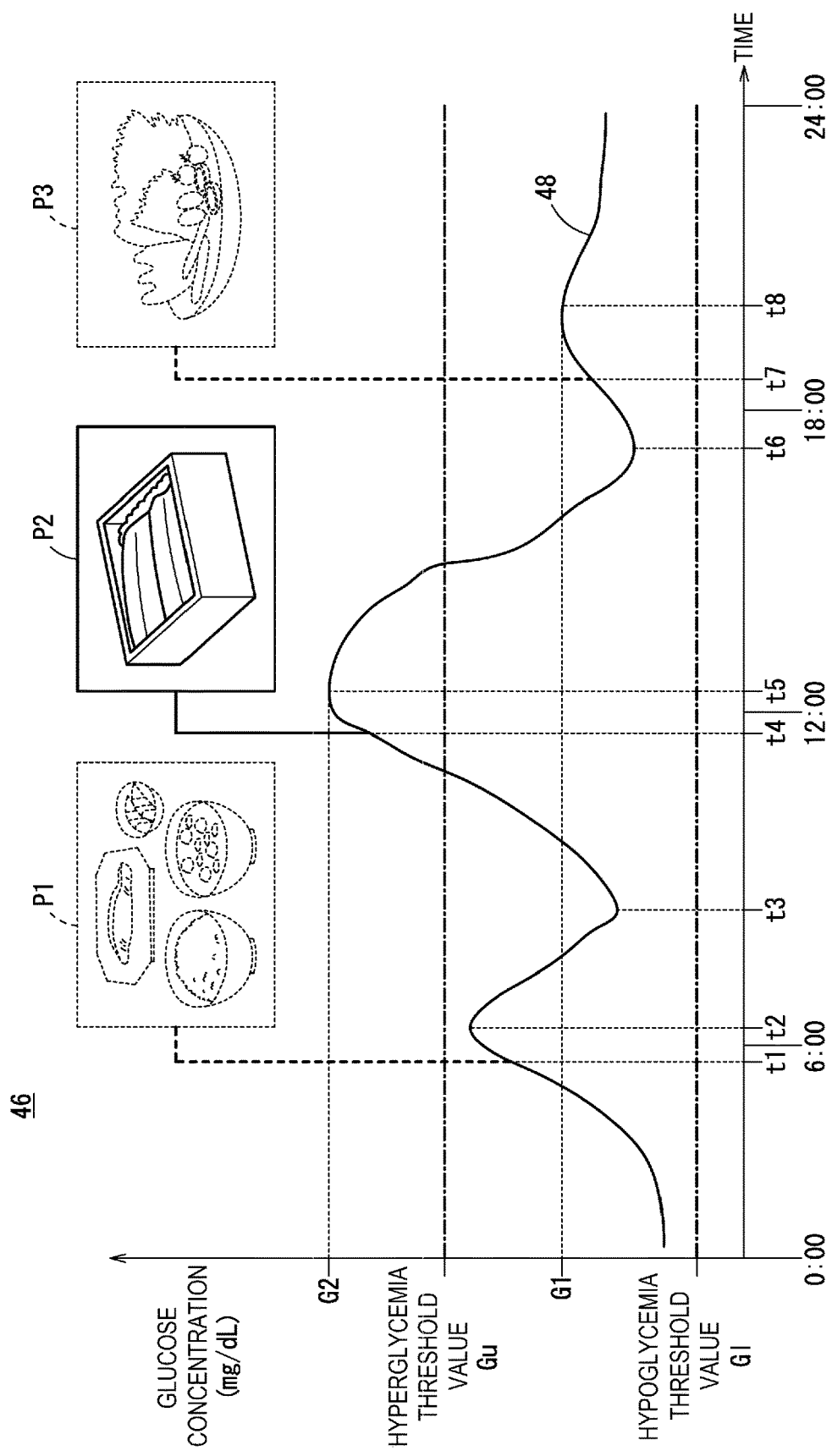

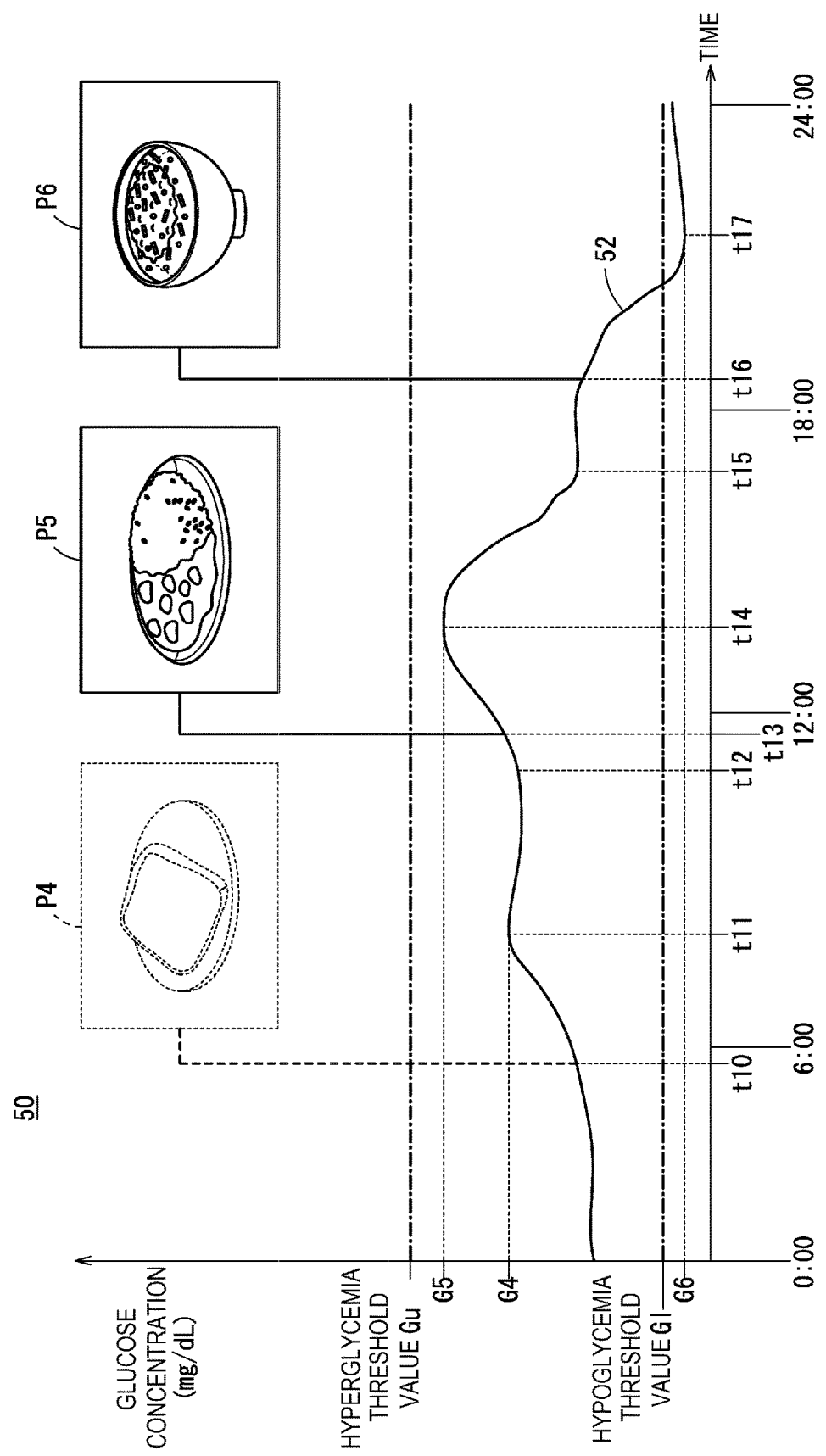
[FIG. 5]

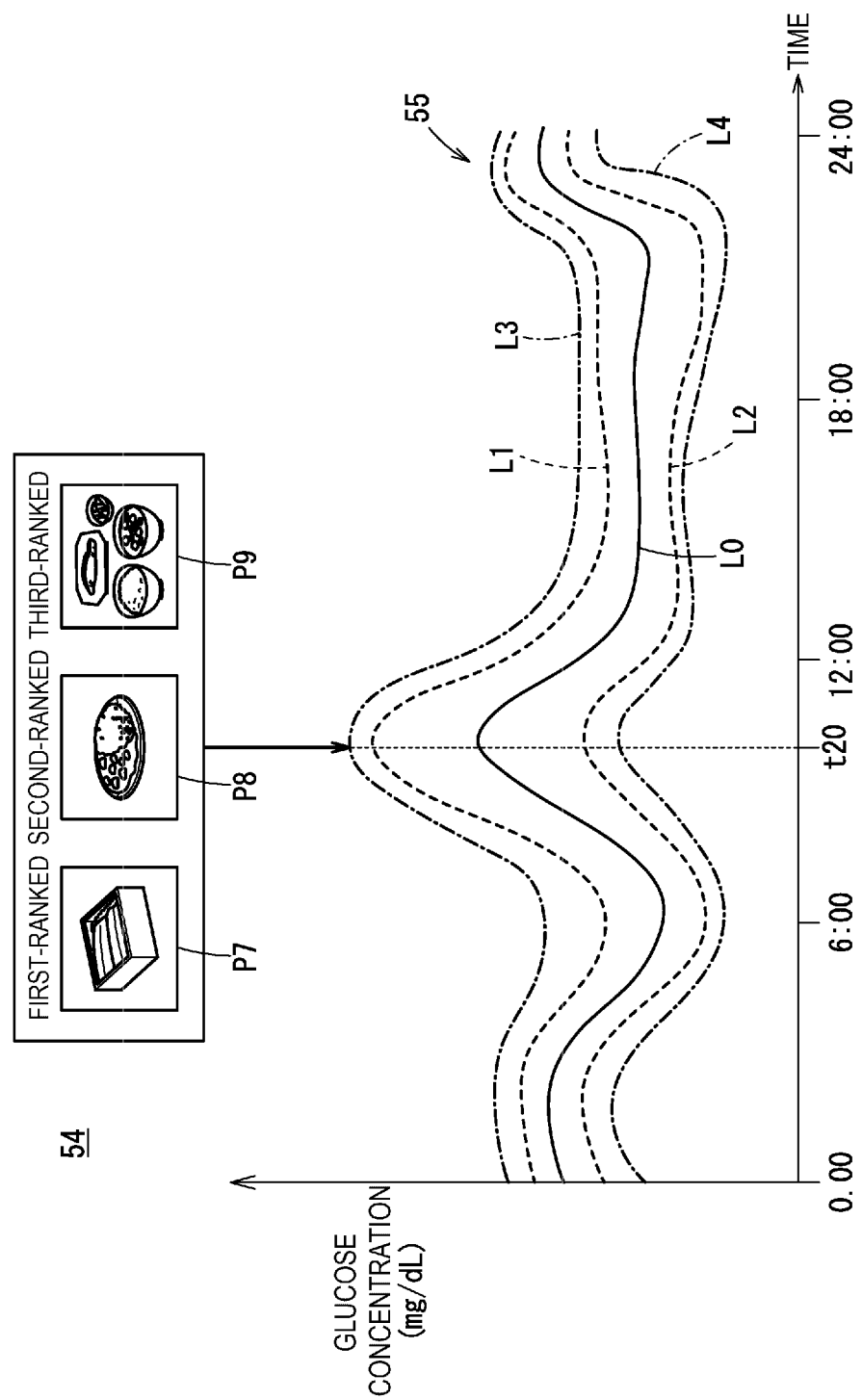
[FIG. 6]

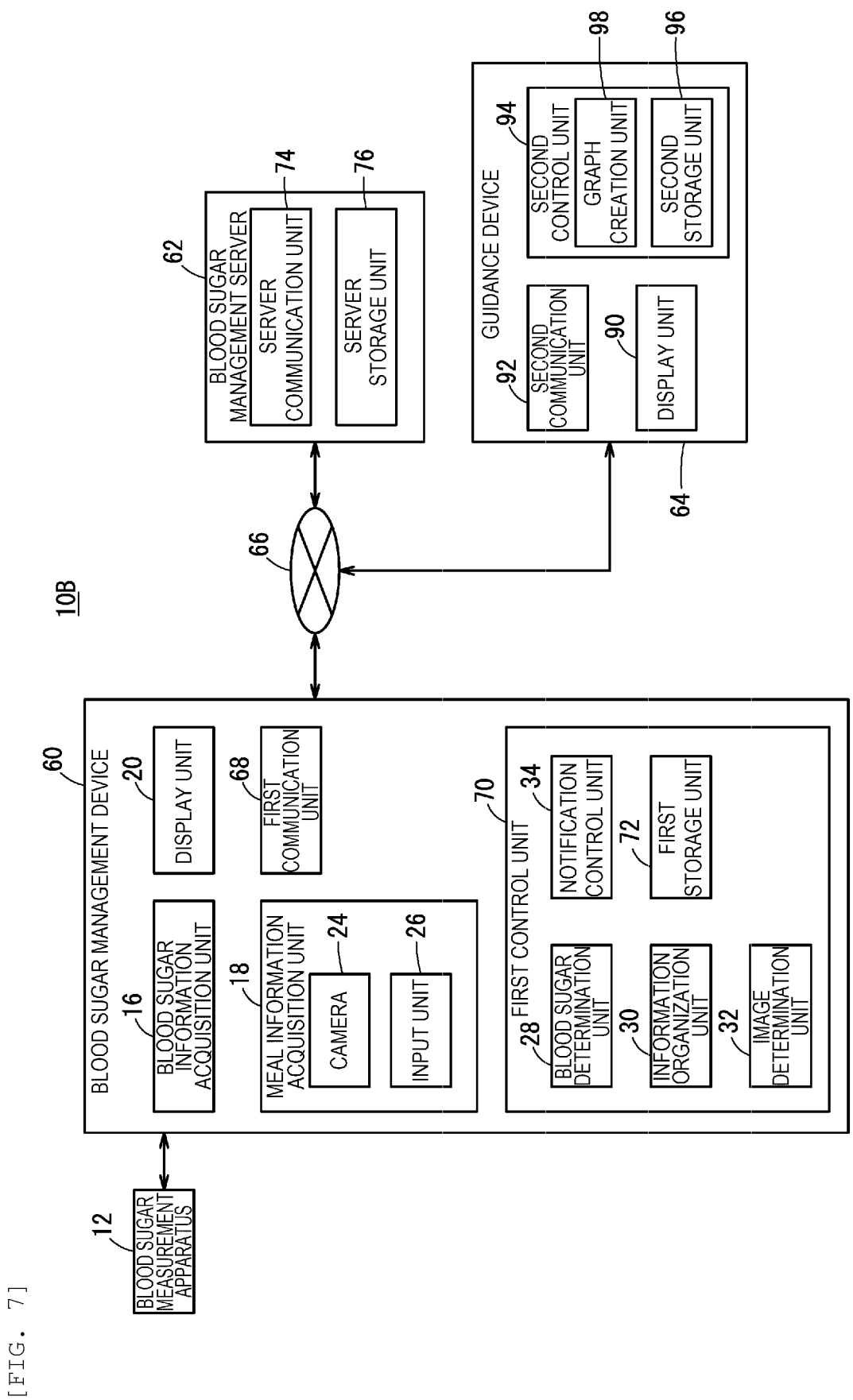
[FIG. 7]

[FIG. 8]
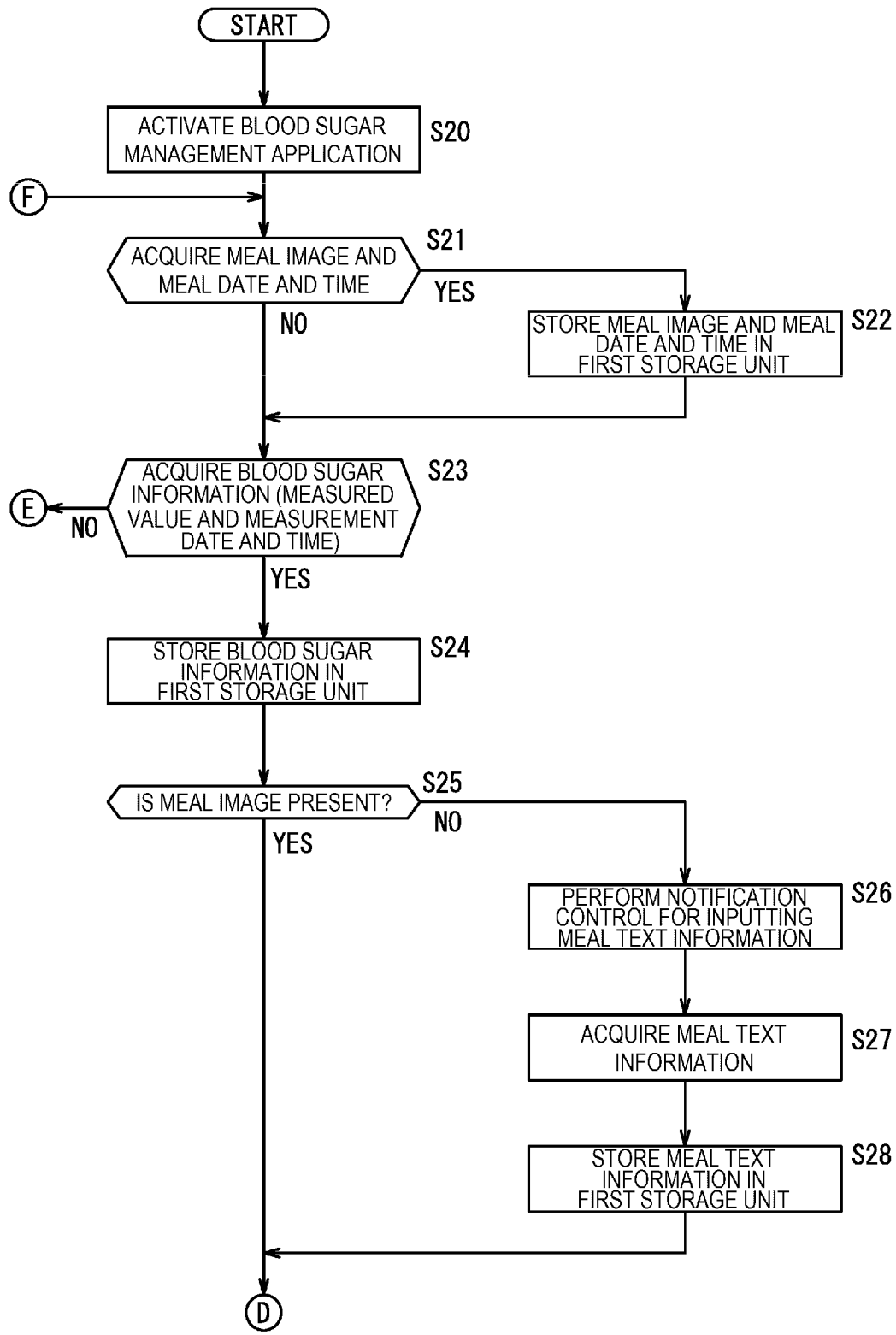

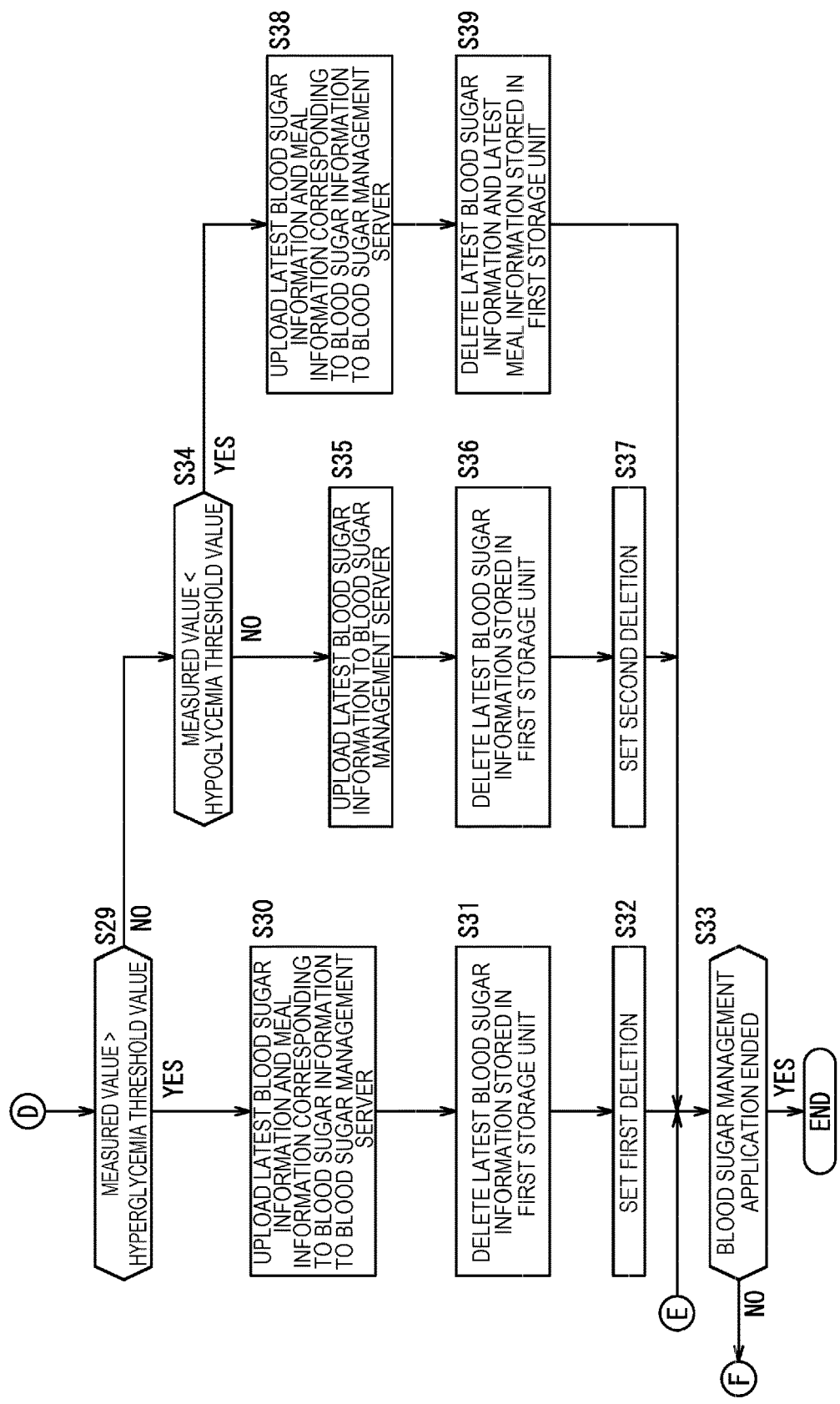
[FIG. 9]

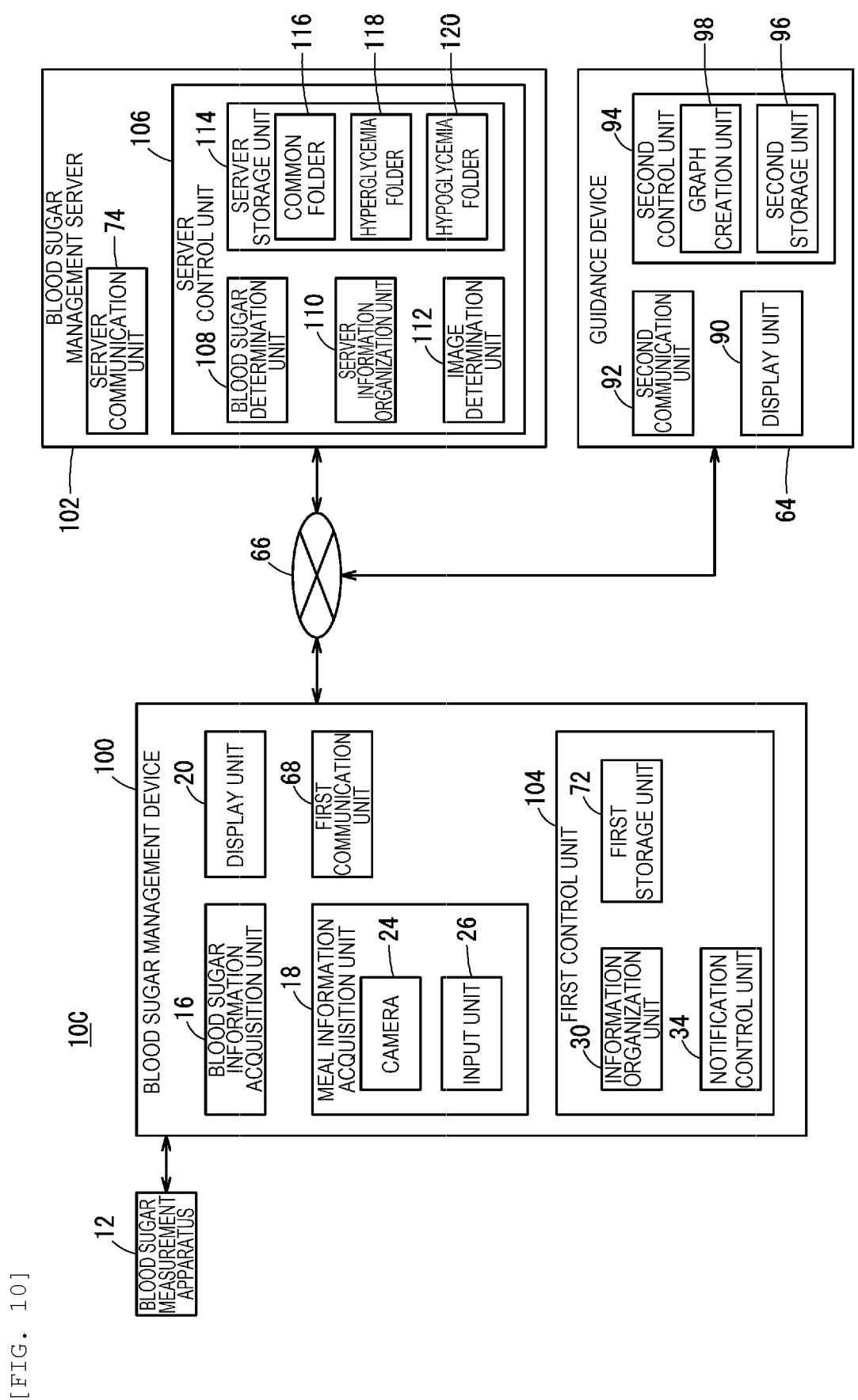
[FIG. 10]

[FIG. 11]
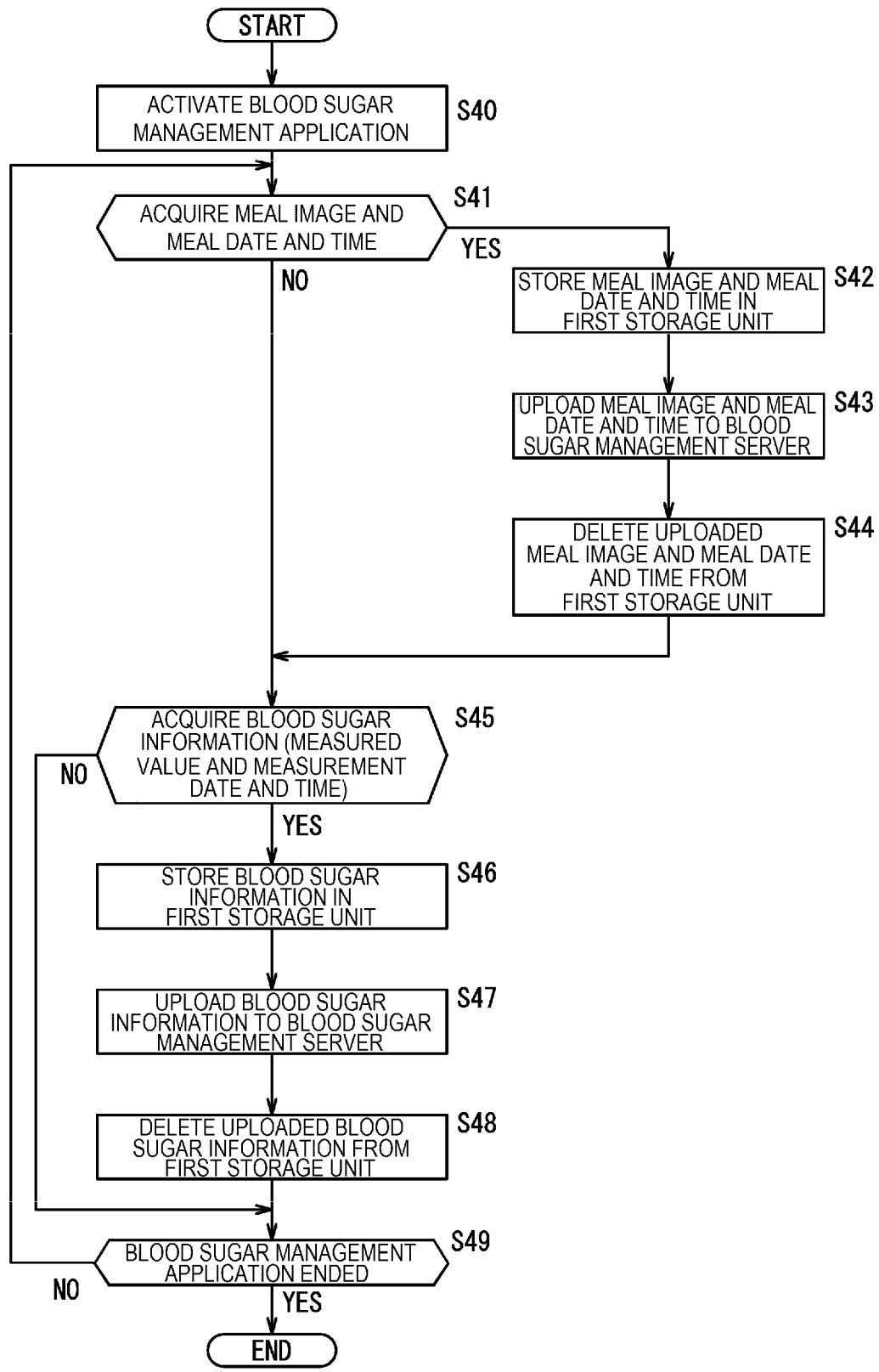

[FIG. 12]
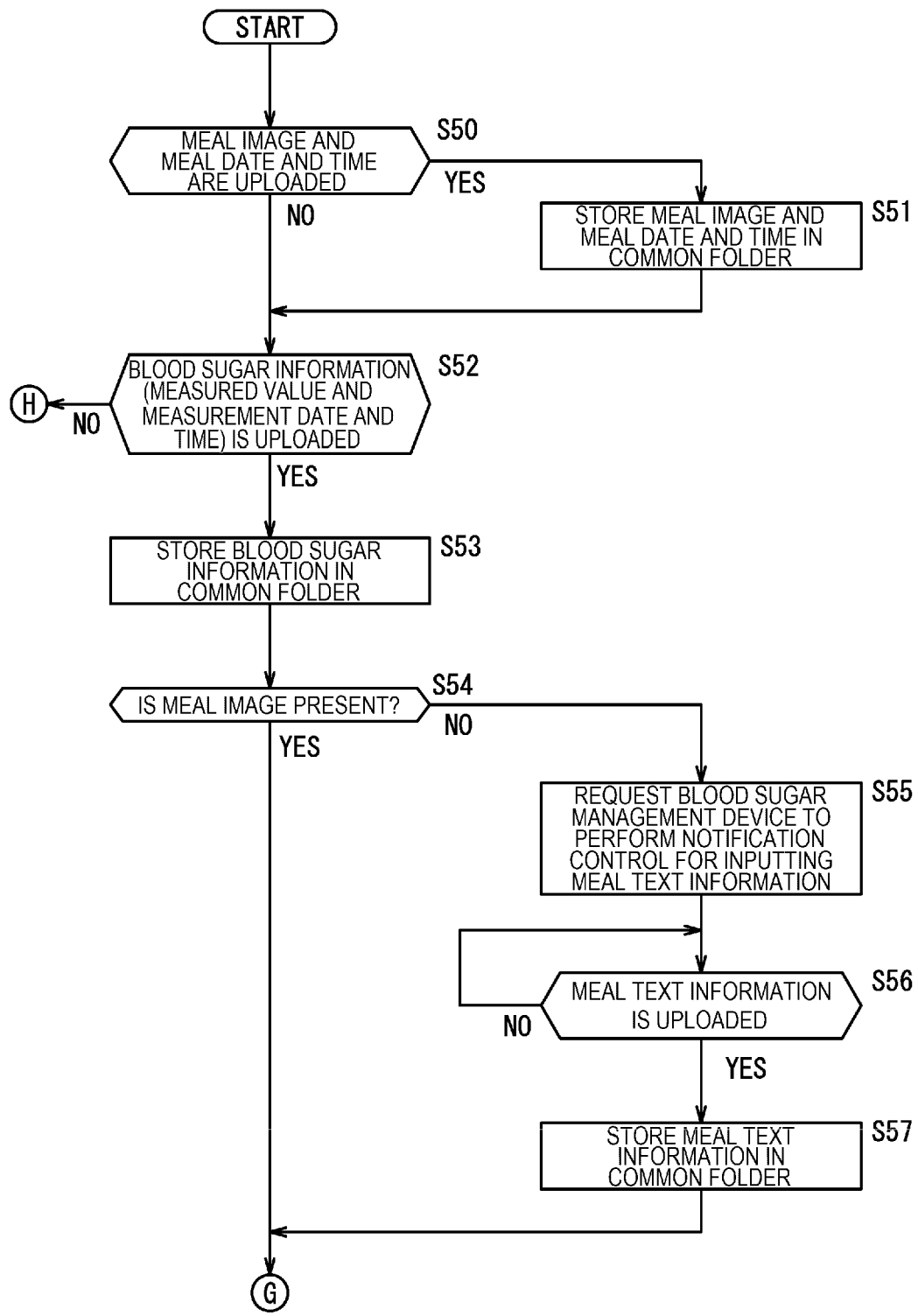

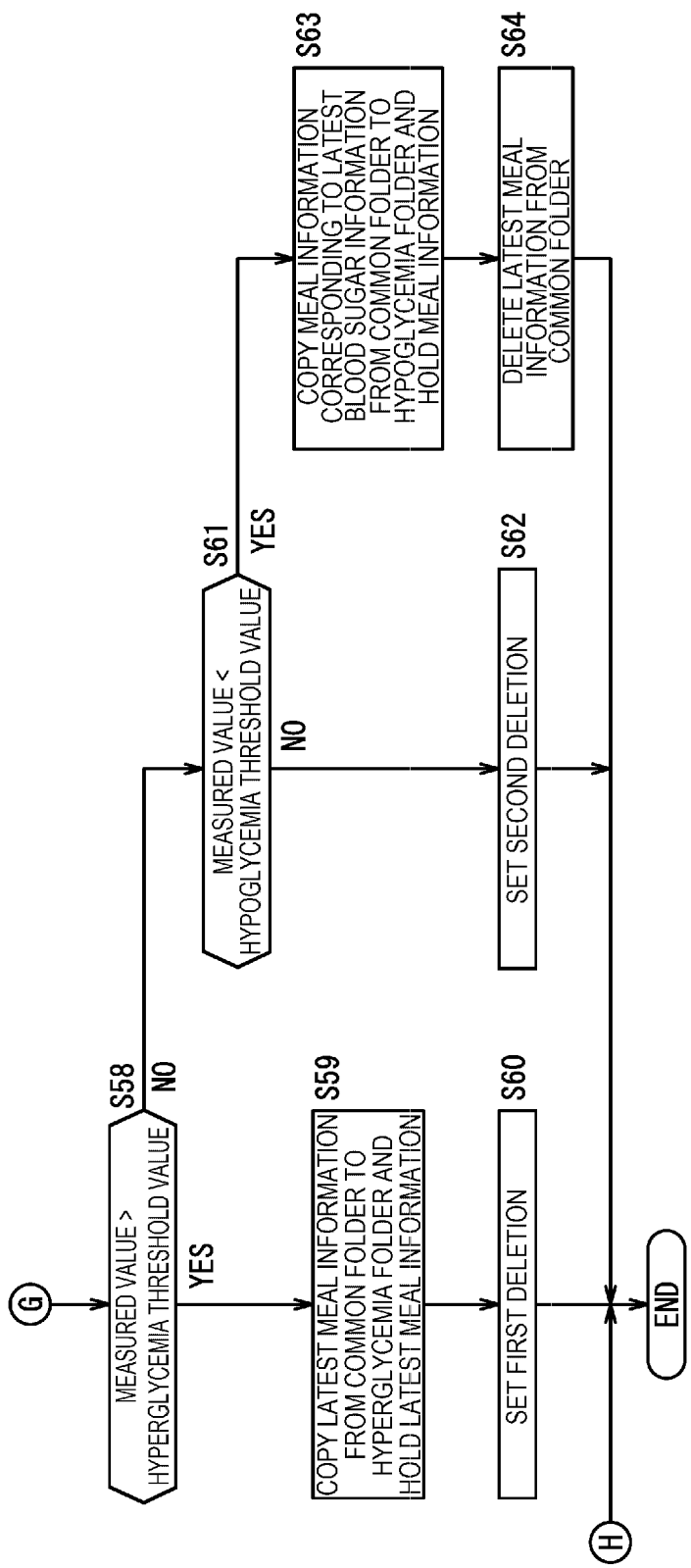
[FIG. 13]

BLOOD SUGAR MANAGEMENT DEVICE, BLOOD SUGAR MANAGEMENT SYSTEM, BLOOD SUGAR MANAGEMENT METHOD, AND BLOOD SUGAR MANAGEMENT PROGRAM

CROSS-REFERENCE TO RELATED APPLICATIONS

This application is a bypass continuation of PCT Application No. PCT/JP2020/031554, filed on Aug. 21, 2020, which claims priority to Japanese Application No. 2019-196828, filed on Oct. 30, 2019. The contents of these applications are hereby incorporated by reference in their entirety.

BACKGROUND

The present disclosure relates to a blood sugar management device, a blood sugar management system, a blood sugar management method, and a blood sugar management program.

JP-A-2019-28625 discloses a blood sugar management system for acquiring blood sugar information including a measured blood sugar value and meal information including a meal image of a subject (blood sugar subject) by a blood sugar management device (user terminal), and uploading the information from the blood sugar management device to a blood sugar management server over a network. In such a blood sugar management system, the blood sugar information and the meal information are stored in each of the blood sugar management device and the blood sugar management server.

SUMMARY

However, in the blood sugar management system, all pieces of the meal information are stored in each of the blood sugar management device and the blood sugar management server. Therefore, there is a problem that the storage capacity required for storing meal information becomes considerably large. In addition, a doctor or a user cannot efficiently find a piece of meal information related to a specific blood-sugar level state from a huge number of pieces of meal information stored in the blood sugar management device and the blood sugar management server.

Certain embodiments of the present disclosure have been developed in consideration of such a problem, and an object of certain embodiments is to provide a blood sugar management device, a blood sugar management system, a blood sugar management method, and a blood sugar management program capable of reducing the storage capacity necessary for storing meal information and effectively performing blood sugar management.

A first aspect of the invention is a blood sugar management device including a blood sugar information acquisition unit configured to acquire blood sugar information including a measured value, and a meal information acquisition unit configured to acquire meal information including a meal image of a subject, the blood sugar management device including a storage unit configured to store the blood sugar information and the meal information, a blood sugar determination unit configured to determine whether or not the measured value is within a predetermined range, and an information organization unit configured to organize the meal information stored in the storage unit, in which based on determination of the blood sugar determination unit, when the blood sugar determination unit determines that the measured value is within the predetermined range, the information organization unit deletes meal information corresponding to the measured value from the storage unit, and when the blood sugar determination unit determines that the measured value is not within the predetermined range, the information organization unit holds meal information corresponding to the measured value in the storage unit.

A second aspect of the invention is a blood sugar management system including a blood sugar management device including a blood sugar information acquisition unit configured to acquire blood sugar information including a measured value, and a meal information acquisition unit configured to acquire meal information including a meal image of a subject, and a blood sugar management server configured to receive the blood sugar information and the meal information uploaded from the blood sugar management device through a network, in which the blood sugar management device includes a storage unit configured to store the blood sugar information and the meal information, a blood sugar determination unit configured to determine whether or not the measured value is within a predetermined range, an information organization unit configured to organize the meal information stored in the storage unit, and a communication unit configured to upload the meal information stored in the storage unit to the blood sugar management server, when the blood sugar determination unit determines that the measured value is not within the predetermined range, the communication unit uploads meal information corresponding to the measured value to the blood sugar management server, and when the blood sugar determination unit determines that the measured value is within the predetermined range, the information organization unit deletes meal information corresponding to the measured value from the storage unit.

A third aspect of the invention is a blood sugar management system including a blood sugar management device including a blood sugar information acquisition unit configured to acquire blood sugar information including a measured value, and a meal information acquisition unit configured to acquire meal information including a meal image of a subject, and a blood sugar management server configured to receive the blood sugar information and the meal information uploaded from the blood sugar management device through a network, in which the blood sugar management device includes a storage unit configured to store the blood sugar information and the meal information, and an information organization unit configured to delete the meal information uploaded from the blood sugar management device to the blood sugar management server from the storage unit, the blood sugar management server includes a server storage unit configured to store the blood sugar information and the meal information uploaded from the blood sugar management device, a blood sugar determination unit configured to determine whether or not the measured value is within a predetermined range, and a server information organization unit configured to organize the meal information stored in the server storage unit, and when the blood sugar determination unit determines that the measured value is within the predetermined range, the server information organization unit deletes meal information corresponding to the measured value from the server storage unit, and when the blood sugar determination unit determines that the measured value is not within the predetermined range, the server information organization unit holds meal information corresponding to the measured value in the server storage unit.

A fourth aspect of the invention is a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a blood sugar determination step of determining whether or not the measured value is within a predetermined range, and an information organization step of organizing the meal information stored in the storage unit, in which, in the information organization step, when the measured value is within the predetermined range, meal information corresponding to the measured value is deleted from the storage unit, and when the measured value is not within the predetermined range, meal information corresponding to the measured value is held in the storage unit.

A fifth aspect of the invention is a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a blood sugar determination step of determining whether or not a measured value of the blood sugar information stored in the storage unit is within a predetermined range, a communication step of uploading meal information corresponding to the measured value to a blood sugar management server when it is determined in the blood sugar determination step that the measured value is not within the predetermined range, and an information organization step of deleting meal information corresponding to the measured value from the storage unit when it is determined in the blood sugar determination step that the measured value is within the predetermined range.

A sixth aspect of the invention is a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a communication step of uploading the blood sugar information and the meal information stored in the storage unit to a blood sugar management server, an information organization step of deleting the meal information uploaded from a blood sugar management device to the blood sugar management server from the storage unit, a server storage step of storing the blood sugar information and the meal information uploaded from the blood sugar management device in a server storage unit, a blood sugar determination step of determining whether or not a measured value of the blood sugar information stored in the server storage unit is within a predetermined range, and a server information organization step of organizing the meal information stored in the server storage unit, in which, in the server information organization step, when it is determined in the blood sugar determination step that the measured value is within the predetermined range, meal information corresponding to the measured value is deleted from the server storage unit, and when it is determined in the blood sugar determination step that the measured value is not within the predetermined range, meal information corresponding to the measured value is held in the server storage unit.

A seventh aspect of the invention is a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a blood sugar determination step of determining whether or not the measured value is within a predetermined range, and an information organization step of organizing the meal information stored in the storage unit, in which, in the information organization step, when the measured value is within the predetermined range, meal information corresponding to the measured value is deleted from the storage unit, and when the measured value is not within the predetermined range, meal information corresponding to the measured value is held in the storage unit.

An eighth aspect of the invention is a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a blood sugar determination step of determining whether or not a measured value of the blood sugar information stored in the storage unit is within a predetermined range, a communication step of uploading meal information corresponding to the measured value to a blood sugar management server when it is determined in the blood sugar determination step that the measured value is not within the predetermined range, and an information organization step of deleting meal information corresponding to the measured value from the storage unit when it is determined in the blood sugar determination step that the measured value is within the predetermined range.

A ninth aspect of the invention is a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a communication step of uploading the blood sugar information and the meal information stored in the storage unit to a blood sugar management server, an information organization step of deleting the meal information uploaded from a blood sugar management device to the blood sugar management server from the storage unit, a server storage step of storing the blood sugar information and the meal information uploaded from the blood sugar management device in a server storage unit, a blood sugar determination step of determining whether or not a measured value of the blood sugar information stored in the server storage unit is within a predetermined range, and a server information organization step of organizing the meal information stored in the server storage unit, in which, in the server information organization step, when it is determined in the blood sugar determination step that the measured value is within the predetermined range, meal information corresponding to the measured value is deleted from the server storage unit, and when it is determined in the blood sugar determination step that the measured value is not within the predetermined range, meal information corresponding to the measured value is held in the server storage unit.

According to certain embodiments of the invention, when a measured value is within a predetermined range, meal information corresponding to the measured value is deleted from the storage unit (server storage unit), and thus the storage capacity necessary to store meal information can be reduced. Further, when the measured value is not within the predetermined range, the meal information corresponding to the measured value is held in the storage unit (server storage unit) (uploaded to the blood sugar management server). In this way, only meal information considered to be particularly necessary for blood sugar management is stored in the storage unit (server storage unit). Therefore, because it is possible to efficiently find meal information related to the glucose concentration not within the predetermined range, blood sugar management can be effectively performed.

BRIEF DESCRIPTION OF THE DRAWINGS

FIG. 1 is a block diagram of a blood sugar management system according to a first embodiment of the invention.

FIG. 2 is a first flowchart describing a blood sugar management method using the blood sugar management system of FIG. 1.

FIG. 3 is a second flowchart describing the blood sugar management method using the blood sugar management system of FIG. 1.

FIG. 4 is a blood sugar management graph according to a first example.

FIG. 5 is a blood sugar management graph according to a second example.

FIG. 6 is a blood sugar management graph according to a third example.

FIG. 7 is a block diagram of a blood sugar management system according to a second embodiment of the invention.

FIG. 8 is a first flowchart describing a blood sugar management method using the blood sugar management system of FIG. 7.

FIG. 9 is a second flowchart describing the blood sugar management method using the blood sugar management system of FIG. 7.

FIG. 10 is a block diagram of a blood sugar management system according to a third embodiment of the invention.

FIG. 11 is a first flowchart describing a blood sugar management method using the blood sugar management system of FIG. 10.

FIG. 12 is a second flowchart describing the blood sugar management method using the blood sugar management system of FIG. 10.

FIG. 13 is a third flowchart describing the blood sugar management method using the blood sugar management system of FIG. 10.

DETAILED DESCRIPTION

Hereinafter, a blood sugar management device, a blood sugar management system, a blood sugar management method, and a blood sugar management program according to certain embodiments of the invention will be described using suitable embodiments with reference to the accompanying drawings.

First Embodiment

A blood sugar management system 10A according to a first embodiment of the invention is for performing blood sugar management on a subject based on blood sugar information including a measured value and meal information including a meal image.

As illustrated in FIG. 1, the blood sugar management system 10A includes a blood sugar measurement apparatus 12 and a blood sugar management device 14.

As the blood sugar measurement apparatus 12, for example, a continuous glucose monitor (CGM) is used. For example, the CGM continuously measures the glucose concentration in an interstitial fluid at regular intervals (for example, every 5 minutes) by a sensor mounted under a skin of a subject (user). The blood sugar measurement apparatus 12 may be a glucometer that measures a blood-sugar level (glucose concentration in plasma) by puncturing a fingertip to cause blood to flow out and taking the blood into a measuring chip. As described above, the blood sugar information mentioned in the invention is a measured value obtained from the subject. More specifically, the measured value includes the blood-sugar level obtained from the blood of the subject and a glucose concentration value that correlates with the blood-sugar level as measured values.

The blood sugar measurement apparatus 12 is configured to be communicable with the blood sugar management device 14. That is, the blood sugar information (measured value, measurement date and time, etc.) obtained by the blood sugar measurement apparatus 12 is transmitted to the blood sugar management device 14.

The blood sugar management device 14 is a device operated by the subject. Examples of the blood sugar management device 14 include a smartphone, a laptop computer, a tablet PC, etc. However, the invention is not limited thereto. The blood sugar management device 14 includes a blood sugar information acquisition unit 16, a meal information acquisition unit 18, a display unit 20, and a control unit 22.

The blood sugar information acquisition unit 16 acquires the blood sugar information transmitted from the blood sugar measurement apparatus 12. At this time, the blood sugar management device 14 and the blood sugar measurement apparatus 12 may be connected wirelessly or by wire. Further, the blood sugar information acquisition unit 16 may acquire the blood sugar information on the blood sugar measurement apparatus 12 via an auxiliary storage apparatus such as a flash memory. Data acquired by the blood sugar information acquisition unit 16 is a measured value obtained by the blood sugar measurement apparatus 12. When the blood sugar measurement apparatus is the CGM, profile information on the continuously observed glucose concentration is included.

The meal information acquisition unit 18 acquires the meal information of the subject. The meal information includes a meal image (meal photograph) of the subject, the meal date and time, and meal text information (meal content memo). The meal information acquisition unit 18 has a camera 24 for acquiring a meal image and an input unit 26 (touch panel, keyboard, mouse, etc.) for acquiring text information, etc.

The display unit 20 may include an LED display, an LCD display, a CRT display, a plasma display, a touch screen display, etc. However, the invention is not limited thereto. The display unit 20 may also serve as the input unit 26 by being configured as a touch screen display, for example. The display unit 20 displays a meal image held in a storage unit 36, which will be described later, together with the measured value.

The control unit 22 is a calculator including a microcomputer, has a CPU (central processing unit), and a ROM, a RAM, etc., which are memories, and functions as various function realization units (function realization means) by the CPU reading and executing a program stored in the ROM. Note that the various function realization units can also each include a function realizer as hardware. Blood sugar management application software (blood sugar management application) for managing the blood-sugar level is installed in the control unit 22.

The control unit 22 includes a blood sugar determination unit 28, an information organization unit 30, an image determination unit 32, a notification control unit 34, the storage unit 36, and a graph creation unit 38.

The blood sugar determination unit 28 determines whether or not the measured value is within a predetermined range (within a normal range) based on the blood sugar information input to the blood sugar information acquisition unit 16. Specifically, the blood sugar determination unit 28 determines whether or not the measured value is higher than a hyperglycemia threshold value. In addition, the blood sugar determination unit 28 determines whether or not the measured value is lower than a hypoglycemia threshold value. Each of the hyperglycemia threshold value and the hypoglycemia threshold value is stored in advance in the storage unit 36. Note that, when the blood sugar measurement apparatus 12 is the CGM, the blood sugar determination unit 28 may be configured to detect a peak value after determining whether or not the measured value is within the predetermined range.

The information organization unit 30 organizes the meal information stored in the storage unit 36. The image determination unit 32 determines whether or not a predetermined meal image is present in the storage unit 36. The notification control unit 34 performs notification control for prompting the subject to input meal text information.

The storage unit 36 has a common folder 40, a hyperglycemia folder 42, and a hypoglycemia folder 44. The common folder 40 stores blood sugar information acquired by the blood sugar information acquisition unit 16 and the meal information acquired by the meal information acquisition unit 18. The hyperglycemia folder 42 stores meal information related to hyperglycemia (glucose concentration higher than the hyperglycemia threshold value). The hypoglycemia folder 44 stores meal information related to hypoglycemia (glucose concentration lower than the hypoglycemia threshold value). Additionally, the storage unit 36 can hold information or a value necessary for determination.

The graph creation unit 38 creates a blood sugar management graph indicating a relationship between the blood sugar information and the meal information based on the blood sugar information and the meal information stored in the storage unit 36.

Next, a blood sugar management method using the blood sugar management system 10A will be described.

As illustrated in FIG. 2, first, the subject activates the blood sugar management application of the blood sugar management device 14 (step S1). The control unit 22 determines whether or not the meal information acquisition unit 18 has acquired the meal image and the meal date and time (step S2). The meal image is acquired by the subject photographing meal content thereof using the camera 24. The meal date and time is acquired by the subject inputting an actual meal date and time (meal start date and time) from the input unit 26 and registering the date and time in the blood sugar management application. Alternatively, the meal date and time may be regarded as a photographing date and time of the meal image, and the photographing date and time of the meal image may be automatically acquired. In this case, the subject can save the trouble of inputting the meal date and time.

When the control unit 22 determines that the meal image and the meal date and time have been acquired (step S2: YES), the information organization unit 30 stores the corresponding meal image and meal date and time in the common folder 40 (step S3). At this time, when there is a plurality of meal images, meal images other than the latest meal image are deleted. In addition, when there is a plurality of meal images, the subject may be allowed to select the most suitable one of the plurality of meal images, so that the selected meal image is left in the common folder 40, and meal images not selected are deleted. Alternatively, when there is a plurality of meal images, the subject may be prompted to photograph the meal image again after deleting all the meal images. In this way, by storing only one meal image for one meal in the storage unit 36, it is possible to prevent the storage capacity of the storage unit 36 from being pressurized by unnecessary meal images. Not limited to these examples, a plurality of meal images corresponding to one meal may be stored in the storage unit 36. In addition, photographs having different subjects in one meal time may be grouped based on a shape and size of a plate, and one meal image for each group may be stored in the storage unit 36 as a plurality of photographs corresponding to one meal. Thereafter, the process proceeds to step S4.

On the other hand, when the control unit 22 determines that the meal image and the meal date and time have not been acquired (step S2: NO), the control unit 22 determines whether or not the blood sugar information acquisition unit 16 has acquired the blood sugar information (measured value and measurement date and time) (step S4). Specifically, when the subject measures the glucose concentration using the blood sugar measurement apparatus 12, blood sugar information including the glucose concentration as a measured value is transmitted from the blood sugar measurement apparatus 12 to the blood sugar information acquisition unit 16. Here, it is determined that the blood sugar information acquisition unit 16 has acquired the blood sugar information. Note that, when the blood sugar measurement apparatus 12 is the CGM, the observed glucose trend is included as the blood sugar information.

When the blood sugar information is not acquired (step S4: NO), the process proceeds to step S13 of FIG. 3. The process of step S13 will be described later. On the other hand, when the determination unit determines that the blood sugar information acquisition unit 16 has acquired the blood sugar information (step S4: YES), the information organization unit 30 stores the blood sugar information in the common folder 40 (step S5).

Subsequently, the image determination unit 32 searches for and determines whether or not the storage unit has a meal image at a meal date and time within a predetermined time (for example, 2 hours) before the measurement date and time of the blood sugar information (step S6). Note that the predetermined time of step S6 is not limited to 2 hours and can be set as appropriate.

When the image determination unit 32 determines that there is no meal image (step S6: NO), the notification control unit 34 performs notification control for prompting the subject to input meal text information (meal content memo and meal date and time) (step S7). Specifically, the notification control unit 34 outputs, for example, a voice saying "Please input meal content within 2 hours from the measurement date and time" from a speaker of the blood sugar management device 14. Further, the notification control unit 34 can display, for example, text "Please input meal content within 2 hours from the measurement date and time" on the display unit 20.

Then, when the meal information acquisition unit 18 acquires meal text information (step S8), the information organization unit 30 saves the meal text information in the common folder 40 (step S9). Thereafter, the process proceeds to step S10 of FIG. 3.

On the other hand, when the image determination unit 32 determines that there is a meal image (step S6: YES in FIG. 2), as illustrated in FIG. 3, the blood sugar determination unit 28 determines whether or not the measured value is higher than the hyperglycemia threshold value (step S10). Note that in step S10, when the blood sugar measurement apparatus 12 is the CGM, the measured value refers to the observed glucose concentration. In this case, when the observed glucose concentration exceeds the hyperglycemia threshold value, the blood sugar determination unit 28 determines that the measured value is higher than the hyperglycemia threshold value. Further, the blood sugar determination unit 28 may specify the highest glucose concentration (peak value) in a time range exceeding the hyperglycemia threshold value and hold the highest glucose concentration as blood sugar information. Note that when the duration of the situation where the hyperglycemia threshold value is exceeded or the situation where the hypoglycemia threshold value is not exceeded exceeds each predetermined value, the blood sugar determination unit 28 may allow meal information to be stored as the hyperglycemia threshold value or the hypoglycemia threshold value. This description is similarly applied to step S14 described later.

When the blood sugar determination unit 28 determines that the measured value is higher than the hyperglycemia threshold value (step S10: YES), the information organization unit 30 copies the latest meal information (meal information corresponding to the measured value) from the common folder 40 to the hyperglycemia folder 42 and holds the latest meal information (step S11).

Then, the information organization unit 30 sets first deletion (step S12). Specifically, the information organization unit 30 sets deletion of the latest meal information stored in the common folder 40. That is, the information organization unit 30 performs setting so that, after a predetermined time (for example, 12 hours) elapses from the meal date and time of the latest meal information stored in the common folder 40, the meal information is deleted. Note that the predetermined time of step S12 is not limited to 12 hours and can be set as appropriate.

Thereafter, the control unit 22 determines whether or not the blood sugar management application has ended (step S13). When the blood sugar management application has ended, the current operation flow is ended. When the blood sugar management application has not ended, the process returns to step S2 of FIG. 2.

On the other hand, when the blood sugar determination unit 28 determines that the measured value is equal to or lower than the hyperglycemia threshold value (step S10: NO), the blood sugar determination unit 28 determines whether or not the measured value is lower than the hypoglycemia threshold value (step S14). When the blood sugar determination unit 28 determines that the measured value is equal to or higher than the hypoglycemia threshold value (step S14: NO), the information organization unit 30 sets second deletion (step S15).

Specifically, in step S15, the information organization unit 30 sets deletion of the latest meal information stored in the common folder 40. That is, the information organization unit 30 performs setting so that, after a predetermined time (for example, 12 hours) elapses from the meal date and time of the latest meal information stored in the common folder 40, the meal information is deleted. Note that the predetermined time of step S15 is not limited to 12 hours and can be set as appropriate. Thereafter, the process proceeds to step S13.

On the other hand, when the blood sugar determination unit 28 determines that the measured value is lower than the hypoglycemia threshold value (step S14: YES), the information organization unit 30 copies the meal information corresponding to the latest blood sugar information from the common folder 40 to the hypoglycemia folder 44 and holds the meal information (step S16). Specifically, the information organization unit 30 copies meal information (for example, meal information for two meals) for a past predetermined time (for example, 12 hours) before the latest measurement date and time from the common folder 40 to the hypoglycemia folder 44 and holds the meal information. Note that the predetermined time of step S16 is not limited to 12 hours and can be set as appropriate. Then, the information organization unit 30 deletes the latest meal information from the common folder 40 (step S17). Thereafter, the process proceeds to step S13. Note that, when blood sugar information lower than the hypoglycemia threshold value is observed again within a predetermined time from step S17, the data held in the hypoglycemia folder 44 may be associated with the latest blood sugar information.

Such a blood sugar management method includes an information acquisition step (step S2 and step S4) of acquiring blood sugar information and meal information, a storage step (step S3 and step S5) of storing the blood sugar information and the meal information acquired in the information acquisition step in the storage unit 36, a blood sugar determination step (step S10 and step S14) of determining whether or not the measured value is within a predetermined range, and an information organization step (step S11, step S12, step S15, and step S16) of organizing the meal information stored in the storage unit 36. In the information organization step, when the measured value is within the predetermined range, the meal information corresponding to the measured value is deleted from the storage unit 36, and when the measured value is not within the predetermined range, the meal information corresponding to the measured value is held in the storage unit 36.

Next, the blood sugar management graph created by the graph creation unit 38 will be described. The graph creation unit 38 creates the blood sugar management graph, for example, by the subject operating a graph creation icon of the blood sugar management application.

The graph creation unit 38 creates a blood sugar management graph based on the measured value and meal information stored in the storage unit 36 using the blood sugar management method described above. Specifically, the graph creation unit 38 creates, for example, a blood sugar management graph 46 illustrated in FIG. 4. As illustrated in FIG. 4, in the blood sugar management graph 46, a meal image is superimposed and displayed on a glucose concentration line 48 indicating a temporal change in a measured value. Note that, in the blood sugar management graph 46, the horizontal axis indicates time, and the vertical axis indicates a measured value (glucose concentration or blood-sugar level).

Specifically, in the blood sugar management graph 46, the glucose concentration reaches a first peak at a time point t2 after a time when a meal image P1 is acquired (a time point t1), and decreases from the time point t2 to a time point t3. Thereafter, the glucose concentration increases from the time point t3, reaches a second peak at a time point t5 after a meal when a next meal image P2 is acquired (a time point t4), and decreases from the time point t5 to a time point t6. Then, the glucose concentration increases from the time point t6, reaches a third peak at a time point t8 after a meal when a meal image P3 is acquired (a time point t7), and decreases from the time point t8.

In such a blood sugar management graph 46, the first peak after the meal at the time point t1 (glucose concentration at the time point t2) is lower than a hyperglycemia threshold value Gu and higher than a hypoglycemia threshold value Gl. In addition, the glucose concentration does not fall below the hypoglycemia threshold value Gl from the time point t1 until a predetermined time (for example, 12 hours) elapses. For this reason, the meal image P1 at the time point t1 is deleted from the storage unit 36 (common folder 40) after the predetermined time elapsed from the time point t1. Therefore, in the blood sugar management graph 46, the meal image P1 is not displayed at the time point t1.

The second peak after the meal at the time point t4 (glucose concentration G2 at the time point t5) is higher than the hyperglycemia threshold value Gu. For this reason, the meal image P2 at the time point t4 is stored in the hyperglycemia folder 42. Therefore, on the blood sugar management graph 46, the meal image P2 is displayed at the time point t4.

The third peak after the meal at the time point t7 (glucose concentration G1 at the time point t8) is lower than the hyperglycemia threshold value Gu and higher than the hypoglycemia threshold value Gl. Then, assuming that the glucose concentration does not fall below the hypoglycemia threshold value Gl from the time point t7 until a predetermined time (for example, 12 hours) elapses, the meal image P3 at the time point t7 is deleted from the common folder 40 after the predetermined time elapses from the time point t7. Therefore, the meal image P3 is not displayed at the time point t7.

In such a blood sugar management graph 46, the meal image P1 at the time point t1 and the meal image P3 at the time point t7 are not displayed, and the meal image P2 at the time point t4 is displayed. For this reason, the meal image P2 presumed to be the cause of hyperglycemia can be efficiently known. In other words, it is possible to save the trouble of searching for the meal image P2, which is presumed to be the cause of hyperglycemia, from a huge number of meal images.

Further, the graph creation unit 38 creates, for example, a blood sugar management graph 50 illustrated in FIG. 5. The blood sugar management graph 50 is created similarly to the blood sugar management graph 46 described above. That is, as illustrated in FIG. 5, in the blood sugar management graph 50, a meal image is superimposed and displayed on a glucose concentration line 52 indicating a temporal change in the glucose concentration.

In the blood sugar management graph 50, the glucose concentration reaches a first peak at a time point t11 after a meal at a time point t10, and gradually decreases from the time point t11 to a time point t12. Thereafter, the glucose concentration increases from the time point t12, reaches a second peak at a time point t14 after a meal at a time point t13, and decreases from the time point t14 to a time point t15. Then, the glucose concentration becomes substantially constant from the time point t15 and decreases again after a meal at a time point t16. Then, at a time point t17, a lower limit is reached.

In such a blood sugar management graph 50, the first peak after the meal at the time point t10 (glucose concentration G4 at the time point t11) is lower than the hyperglycemia threshold value Gu and higher than the hypoglycemia threshold value Gl. Further, the glucose concentration G4 does not fall below the hypoglycemia threshold value Gl from the time point t10 until a predetermined time (for example, 12 hours) elapses. For this reason, a meal image P4 at the time point t10 is deleted from the common folder 40 after the predetermined time elapses from the time point t10. Therefore, the meal image P4 is not displayed at the time point t10.

The second peak after the meal at the time point t13 (glucose concentration G5 at the time point t14) is lower than the hyperglycemia threshold value Gu and higher than the hypoglycemia threshold value Gl. Further, a lower limit at the time point t17 after the meal at the time point t16 (glucose concentration G6 at the time point t17) is lower than the hypoglycemia threshold value Gl. Note that the time point t17 is before a predetermined time (for example, 12 hours) elapses from the time point t13.

In this case, all meal images for a predetermined time (for example, 12 hours) (meal image P5 at time point t13 and meal image P6 at time point t16) before the time point t17 are stored in the hypoglycemia folder 44. Therefore, the meal image P5 is displayed at the time point t13, and the meal image P6 is displayed at the time point t16.

In such a blood sugar management graph 50, the meal image P4 at the time point t10, which is a predetermined time or more before the time point t17, is not displayed, and the meal image P5 at the time point t13 and the meal image P6 at the time point t16 are displayed. Hypoglycemia occurs not only by a state immediately before the onset of hypoglycemia but also by a blood sugar state before the state. That is, it is necessary to consider an influence at a predetermined time before (for example, 12 hours before) a time point when hypoglycemia occurs. For this reason, in the blood sugar management graph 50, the meal images P5 and P6 presumed to be the cause of hypoglycemia are efficiently acquired. In this way, in addition to meal information immediately before a time point when a hypoglycemia level is observed, meal information a long time ago can be further acquired and displayed, and thus the cause of the occurrence of hypoglycemia can be investigated.

The graph creation unit 38 may create, for example, a blood sugar management graph 54 illustrated in FIG. 6. As illustrated in FIG. 6, in this blood sugar management graph 54, a meal image is superimposed and displayed on a blood-sugar level profile 55 (AGP: Ambulatory Glucose Profile) indicating a fluctuation of a blood-sugar level for one day (24 hours) created based on the glucose concentration for a predetermined number of days (for example, one month).

The blood-sugar level profile 55 has a median line L0, a first upper line L1, a first lower line L2, a second upper line L3, and a second lower line L4. The median line L0 indicates a median value of the glucose concentration for the predetermined number of days in each time zone. A band between the first upper line L1 and the first lower line L2 indicates a region in which a first ratio of the glucose concentration for the predetermined number of days in each time zone is present. For example, the region in which the first ratio is present is in the 25th to 75th percentiles. A band between the second upper line L3 and the second lower line L4 indicates a region in which a second ratio of the glucose concentration for the predetermined number of days in each time zone (for example, 10th to 95th percentile) is present. Note that the first ratio and the second ratio can be set as appropriate.

In this blood sugar management graph 54, it is found that the glucose concentration tends to peak at a time point t20 in a day. Then, in the blood sugar management graph 54, meal images P7 to P9 until a predetermined time before (for example, 2 hours before) the time point t20 are displayed in a ranking format.

The first-ranked meal image P7 is a meal image of the day when the glucose concentration is the highest at the time point t20 in a meal image group until the predetermined time before the time point t20 in a data acquisition period. The second-ranked meal image P8 is a meal image of the day when the glucose concentration is the second highest at the time point t20 in the meal image group until the predetermined time before the time point t20. The third-ranked meal image P9 is a meal image of the day when the glucose concentration is the third highest at the time point t20 in the meal image group until the predetermined time before the time point t20. Note that, in this case, the time point t20 may be a predetermined time width instead of a specific time. In this way, by displaying the meal images in descending order of the glucose concentration associated with the meal, it becomes easier to understand the influence of the meal content on the glucose concentration.

Note that, in the blood sugar management graph 54, referring to a time point (not illustrated) when the glucose concentration tends to reach the lower limit in a day, meal images until a predetermined time before the time point may be displayed in a ranking format.

The blood sugar management system 10A according to the present embodiment has the following effects.

The blood sugar management device 14 includes the storage unit 36 that stores blood sugar information and meal information, the blood sugar determination unit 28 that determines whether or not a measured value is within a predetermined range, and the information organization unit 30 that organizes the meal information stored in the storage unit 36. When the blood sugar determination unit determines that the measured value is within the predetermined range, the information organization unit 30 deletes meal information corresponding to the measured value from the storage unit 36. When the blood sugar determination unit 28 determines that the measured value is not within the predetermined range, the information organization unit 30 holds meal information corresponding to the measured value in the storage unit 36. That is, a type of measured value and meal information can be classified after being associated with each other.

According to such a configuration, when the measured value is within the predetermined range, the meal information corresponding to the measured value is deleted from the storage unit 36, so that the storage capacity of the storage unit 36 necessary for storing the meal information can be reduced. Further, when the measured value is not within the predetermined range, the meal information corresponding to the measured value is held in the storage unit 36. In this way, only the meal information considered to be particularly necessary for blood sugar management is stored in the storage unit 36. Therefore, because it is possible to efficiently find meal information related to the glucose concentration that is not within a predetermined range (for example, within a normal range), blood sugar management can be effectively performed.

The blood sugar determination unit 28 determines whether or not the measured value is higher than the hyperglycemia threshold value, and when the blood sugar determination unit 28 determines that the measured value is higher than the hyperglycemia threshold value, the information organization unit 30 holds the meal information corresponding to the measured value in the storage unit 36.

According to such a configuration, meal information related to hyperglycemia can be efficiently known.

The blood sugar determination unit 28 determines whether or not the measured value is lower than the hypoglycemia threshold value, and when the blood sugar determination unit 28 determines that the measured value is lower than the hypoglycemia threshold value, the information organization unit 30 holds the meal information corresponding to the measured value in the storage unit 36.

According to such a configuration, meal information related to hypoglycemia can be efficiently known.

The blood sugar management device 14 includes the display unit 20 that displays the meal image held in the storage unit 36 together with the measured value.

According to such a configuration, the subject can effectively perform blood sugar management by the measured value and the meal image displayed on the display unit 20.

The blood sugar management device 14 includes the image determination unit 32 that determines whether or not the storage unit 36 has a meal image at a meal date and time within a predetermined time before a measurement date and time of blood sugar information, and the notification control unit 34 that performs notification control for prompting the subject to input text information (meal text information) of a meal corresponding to a measured value when the image determination unit 32 determines that the storage unit 36 does not have the meal image.

According to such a configuration, even when the subject forgets to photograph a meal corresponding to a measured value, it is possible to acquire meal text information corresponding to the measured value. That is, the measured value and the meal text information can be associated with each other.

In the blood sugar management method using the blood sugar management system 10A described above, when a measured value is not within a predetermined range (lower than or equal to the hyperglycemia threshold value or higher than or equal to the hypoglycemia threshold value), meal information on the common folder 40 is copied to the hyperglycemia folder 42 or the hypoglycemia folder 44. However, in the blood sugar management method, when the measured value is not within the predetermined range, the meal information corresponding to the measured value may be flagged. When a flag is set in this way, the hyperglycemia folder 42 and the hypoglycemia folder 44 become unnecessary.

Second Embodiment

Next, a blood sugar management system 10B according to a second embodiment of the invention will be described. Note that the same components as those of the blood sugar management system 10A according to the above-described embodiment are designated by the same reference numerals, and detailed description thereof will be omitted.

As illustrated in FIG. 7, the blood sugar management system 10B includes a blood sugar measurement apparatus 12, a blood sugar management device 60, a blood sugar management server 62, and a guidance device 64. The blood sugar management device 60, the blood sugar management server 62, and the guidance device 64 can communicate with each other through a network 66 such as the Internet.

The blood sugar management device 60 is a device operated by the subject. Examples of the blood sugar management device 60 include a smartphone, a laptop computer, a tablet PC, etc. However, the invention is not limited thereto. The blood sugar management device 60 includes a blood sugar information acquisition unit 16, a meal information acquisition unit 18, a display unit 20, a first communication unit 68, and a first control unit 70. The first communication unit 68 uploads (transmits) blood sugar information and meal information to the blood sugar management server 62 through the network 66.

The first control unit 70 is a calculator including a microcomputer, has a CPU, and a ROM, a RAM, etc., which are memories, and functions as various function realization units (function realization means) by the CPU reading and executing a program stored in the ROM. Note that the various function realization units can also each include a function realizer as hardware. The first control unit 70 includes a blood sugar determination unit 28, an information organization unit 30, an image determination unit 32, a notification control unit 34, and a first storage unit 72. The first storage unit 72 stores blood sugar information and meal information. Note that the first control unit 70 corresponds to the control unit 22 in the first embodiment, and the first storage unit 72 corresponds to the storage unit 36 in the first embodiment.

The blood sugar management server 62 includes a server communication unit 74 and a server storage unit 76. The server communication unit 74 receives the blood sugar information and the meal information uploaded from the first communication unit 68. The server storage unit 76 stores the blood sugar information and the meal information received by the server communication unit 74.

The guidance device 64 is a device operated by a medical worker (doctor, registered dietitian, etc.) and is used for performing blood sugar management (treatment guidance, health guidance, etc.) of a subject. The guidance device 64 includes a display unit 90, a second communication unit 92, and a second control unit 94. The display unit 90 is configured similarly to the display unit 20 of the blood sugar management device 60 described above. The second communication unit 92 downloads the blood sugar information and the meal information from the blood sugar management server 62 through the network 66.

The second control unit 94 is a calculator including a microcomputer, has a CPU, and a ROM, a RAM, etc., which are memories, and functions as various function realization units (function realization means) by the CPU reading and executing a program stored in the ROM. Note that the various function realization units can also each include a function realizer as hardware.

The second control unit 94 includes a second storage unit 96 and a graph creation unit 98. The second storage unit 96 stores the blood sugar information and the meal information downloaded from the blood sugar management server 62 by the second communication unit 92. The graph creation unit 98 creates a blood sugar management graph based on the blood sugar information and the meal information stored in the second storage unit 96.

Next, a blood sugar management method using the blood sugar management system 10B according to the present embodiment will be described. The process from step S20 to step S28 of the operation flow illustrated in FIG. 8 is similar to the process from step S1 to step S9 of the operation flow, which is illustrated in FIG. 2, of the blood sugar management system 10A described above. Therefore, the description of the process of steps S20 to S28 will be omitted.

When the first control unit 70 determines that the first storage unit 72 has a meal image (step S25: YES) in step S25 of FIG. 8, as illustrated in FIG. 9, the blood sugar determination unit 28 determines whether or not a measured value is higher than the hyperglycemia threshold value (step S29). Note that, in step S29, when the blood sugar measurement apparatus 12 is a CGM, the glucose concentration is continuously acquired as a measured value. When the blood sugar measurement apparatus 12 is a glucometer, the measured value refers to a measured value measured within a predetermined time after a meal (for example, 2 hours after a meal). This description is similarly applied to step S34 described later.

When the blood sugar determination unit 28 determines that the measured value is higher than a hyperglycemia threshold value (step S29: YES), the first communication unit 68 uploads latest blood sugar information and meal information (latest meal information) corresponding to the blood sugar information to the blood sugar management server 62 (step S30). The blood sugar information and the meal information uploaded to the blood sugar management server 62 in step S30 are stored in the server storage unit 76. Note that, when the blood sugar measurement apparatus 12 is a CGM, and when the observed glucose concentration exceeds the hyperglycemia threshold value, the blood sugar determination unit 28 determines that the measured value is higher than the hyperglycemia threshold value. Further, the blood sugar determination unit 28 may use the highest glucose concentration in a time range exceeding the hyperglycemia threshold value as blood sugar information.

Thereafter, the information organization unit 30 deletes the latest blood sugar information stored in the first storage unit 72 (step S31). In addition, the information organization unit 30 sets first deletion (step S32). Specifically, the information organization unit 30 sets deletion of the latest meal information stored in the first storage unit 72. That is, the information organization unit 30 performs setting so that, after a predetermined time (for example, 12 hours) elapses from a meal date and time of the latest meal information stored in the first storage unit 72, the meal information is deleted. Note that the predetermined time of step S32 is not limited to 12 hours and can be set as appropriate.

Thereafter, the first control unit 70 determines whether or not the blood sugar management application has ended (step S33). When the blood sugar management application has ended, the current operation flow is ended. When the blood sugar management application has not ended, the process returns to step S21 of FIG. 8.

When the blood sugar determination unit 28 determines that the measured value is equal to or lower than the hyperglycemia threshold value (step S29: NO), the blood sugar determination unit 28 determines whether or not the measured value is lower than the hypoglycemia threshold value (step S34). When the blood sugar determination unit 28 determines that the measured value is equal to or higher than the hypoglycemia threshold value (step S34: NO), the first communication unit 68 uploads the latest blood sugar information to the blood sugar management server 62 (step S35). The blood sugar information uploaded to the blood sugar management server 62 in step S35 is stored in the server storage unit 76.

Subsequently, the information organization unit 30 deletes the latest blood sugar information stored in the first storage unit 72 (step S36). In addition, the information organization unit 30 sets second deletion (step S37). Specifically, the information organization unit 30 sets deletion of the latest meal information stored in the first storage unit 72. That is, the information organization unit 30 performs setting so that, after a predetermined time (for example, 12 hours) elapses from the meal date and time of the latest meal information stored in the first storage unit 72, the meal information is deleted. Note that the predetermined time of step S37 is not limited to 12 hours and can be set as appropriate. Thereafter, the process proceeds to step S33.

When the blood sugar determination unit 28 determines that the measured value is lower than the hypoglycemia threshold value (step S34: YES), the first communication unit 68 uploads the latest blood sugar information and meal information corresponding to the blood sugar information to the blood sugar management server 62 (step S38). Note that, here, when the blood sugar measurement apparatus 12 is a CGM, and when the observed glucose concentration becomes lower than the hypoglycemia threshold value, the blood sugar determination unit 28 determines that the measured value is lower than the hypoglycemia threshold value. The blood sugar information and the meal information uploaded to the blood sugar management server 62 in step S38 are stored in the server storage unit 76. Then, the information organization unit 30 deletes the latest blood sugar information and the latest meal information stored in the first storage unit 72 (step S39). Thereafter, the process proceeds to step S33.

In the present embodiment, the medical worker can operate the guidance device 64 to download the blood sugar information and the meal information from the blood sugar management server 62. In this case, the graph creation unit 98 can create the blood sugar management graphs 46, 50, and 54 described above (see FIGS. 4 to 6). In this way, the medical worker can efficiently know meal information related to hyperglycemia and meal information related to hypoglycemia based on the created blood sugar management graphs 46, 50, and 54. For this reason, the medical worker can effectively perform blood sugar management (treatment guidance, health guidance, etc.) using the blood sugar management graphs.

Such a blood sugar management method includes an information acquisition step (step S21 and step S23) of acquiring blood sugar information and meal information, a storage step (step S22 and step S24) of storing the blood sugar information and the meal information acquired in the information acquisition step in the first storage unit 72, a blood sugar determination step (step S29 and step S34) of determining whether or not the measured value is within a predetermined range, a communication step (step S30 and step S38) of uploading meal information corresponding to the measured value to the blood sugar management server 62 when it is determined in the blood sugar determination step that the measured value of the blood sugar information stored in the first storage unit 72 is not within the predetermined range, and an information organization step (step S37) of deleting the meal information corresponding to the measured value from the first storage unit 72 when it is determined in the blood sugar determination step that the measured value is within the predetermined range.

In the blood sugar management method, when upload of the meal information from the blood sugar management device 60 to the blood sugar management server 62 fails, the meal information may be held in the first storage unit 72 of the blood sugar management device 60, and when next meal information is uploaded to the blood sugar management server 62, the previous meal information may be uploaded together. In this case, an upper limit of the capacity of meal information (for example, the number of meal images) held in the first storage unit 72 of the blood sugar management device 60 may be set, and when the upper limit is exceeded, meal information may be deleted in order from the oldest one.

The blood sugar management system 10B according to the present embodiment has the following effects.

The blood sugar management system 10B includes the blood sugar management device 60 and the blood sugar management server 62. The blood sugar management device 60 includes the first storage unit 72 that stores the blood sugar information and the meal information, the blood sugar determination unit 28 that determines whether or not the measured value is within the predetermined range, the information organization unit 30 that organizes the meal information stored in the first storage unit 72, and the first communication unit 68 that uploads the meal information stored in the first storage unit 72 to the blood sugar management server 62. When the blood sugar determination unit 28 determines that the measured value is not within the predetermined range, the first communication unit 68 uploads the meal information corresponding to the measured value to the blood sugar management server 62. When the blood sugar determination unit 28 determines that the measured value is within the predetermined range, the information organization unit 30 deletes the meal information corresponding to the measured value from the first storage unit 72.

According to such a configuration, when the measured value is within the predetermined range, the meal information corresponding to the measured value is deleted from the first storage unit 72, so that the storage capacity of the first storage unit 72 necessary for storing the meal information can be reduced. Further, when the measured value is not within the predetermined range, the meal information corresponding to the measured value is uploaded to the blood sugar management server 62. In this way, only meal information considered to be particularly necessary for blood sugar management is uploaded to the blood sugar management server 62. Therefore, it is possible to efficiently find meal information related to the glucose concentration not within a predetermined range (for example, within a normal range), and thus blood sugar management can be effectively performed.

The blood sugar determination unit 28 determines whether or not the measured value is higher than the hyperglycemia threshold value, and when the blood sugar determination unit 28 determines that the measured value is higher than the hyperglycemia threshold value, the first communication unit 68 uploads the meal information corresponding to the measured value to the blood sugar management server 62.

According to such a configuration, it is possible to efficiently know meal information related to hyperglycemia.

When the blood sugar determination unit 28 determines that the measured value is higher than the hyperglycemia threshold value, after meal information corresponding to the measured value is uploaded to the blood sugar management server 62, the information organization unit 30 deletes the meal information from the first storage unit 72.

According to such a configuration, it is possible to reduce the storage capacity of the first storage unit 72 for storing meal information.

The blood sugar determination unit 28 determines whether or not the measured value is lower than the hypoglycemia threshold value, and when the blood sugar determination unit 28 determines that the measured value is lower than the hypoglycemia threshold value, the first communication unit 68 uploads meal information corresponding to the measured value to the blood sugar management server 62.

According to such a configuration, it is possible to efficiently know meal information related to hypoglycemia.

When the blood sugar determination unit 28 determines that the measured value is lower than the hypoglycemia threshold value, after meal information corresponding to the measured value is uploaded to the blood sugar management server 62, the information organization unit 30 deletes the meal information from the first storage unit 72.

According to such a configuration, the storage capacity of the first storage unit 72 for storing meal information can be further reduced.

Third Embodiment

Next, a blood sugar management system 10C according to a third embodiment of the invention will be described. Note that the same components as those of the blood sugar management systems 10A and 10B according to the above-described embodiments are designated by the same reference numerals, and detailed description thereof will be omitted.

As illustrated in FIG. 10, the blood sugar management system 10C includes a blood sugar measurement apparatus 12, a blood sugar management device 100, a blood sugar management server 102, and a guidance device 64. The blood sugar management device 100, the blood sugar management server 102, and the guidance device 64 can communicate with each other through a network 66 such as the Internet.

The blood sugar management device 100 is a device operated by the subject. Examples of the blood sugar management device 100 include a smartphone, a laptop computer, a tablet PC, etc. However, the invention is not limited thereto. The blood sugar management device 100 includes a blood sugar information acquisition unit 16, a meal information acquisition unit 18, a display unit 20, a first communication unit 68, and a first control unit 104. The first control unit 104 is configured similarly to the first control unit 70 described above, except that the blood sugar determination unit 28 and the image determination unit 32 are not included. The blood sugar management device 100 transmits blood sugar information and meal information to the blood sugar management server 102 through the network 66.

The blood sugar management server 102 includes a server communication unit 74 and a server control unit 106. The server control unit 106 is a calculator including a microcomputer, has a CPU, and a ROM, a RAM, etc., which are memories, and functions as various function realization units (function realization means) by the CPU reading and executing a program stored in the ROM. Note that the various function realization units can also each include a function realizer as hardware.

The server control unit 106 includes a blood sugar determination unit 108, a server information organization unit 110, an image determination unit 112, and a server storage unit 114.

The blood sugar determination unit 108 determines whether or not a measured value is within a predetermined range (within a normal range) based on blood sugar information input to the blood sugar information acquisition unit 16. That is, the blood sugar determination unit 108 determines whether or not the measured value is higher than a hyperglycemia threshold value. Further, the blood sugar determination unit 108 determines whether or not the measured value is lower than a hypoglycemia threshold value. Each of the hyperglycemia threshold value and the hypoglycemia threshold value is stored in advance in the server storage unit 114. Note that, when the blood sugar measurement apparatus 12 is a CGM, and when the observed glucose concentration exceeds the hyperglycemia threshold value, the blood sugar determination unit 108 determines that the measured value is higher than the hyperglycemia threshold value. Further, the blood sugar determination unit 108 may set the highest glucose concentration in a time range exceeding the hyperglycemia threshold value as the measured value and set a date and time when the highest glucose concentration is observed as a measurement date and time.

The server information organization unit 110 organizes meal information stored in the server storage unit 114. The image determination unit 112 determines whether or not a predetermined meal image is present in the storage unit 114.

The server storage unit 114 has a common folder 116, a hyperglycemia folder 118, and a hypoglycemia folder 120. The blood sugar information and the meal information uploaded from the blood sugar management device 100 are stored in the common folder 116. The hyperglycemia folder 118 stores meal information related to hyperglycemia (glucose concentration higher than the hyperglycemia threshold value). The hypoglycemia folder 120 stores meal information related to hypoglycemia (glucose concentration lower than the hypoglycemia threshold value).

Next, a blood sugar management method using the blood sugar management system 10C according to the present embodiment will be described. First, an operation flow of the blood sugar management device 100 will be described.

As illustrated in FIG. 11, when the subject activates a blood sugar management application of the blood sugar management device 100 (step S40), the first control unit 104 determines whether or not the meal information acquisition unit 18 has acquired a meal image and a meal date and time (step S41). The process of step S41 is similar to the process of step S2 described above.

When the first control unit 104 determines that the meal information acquisition unit 18 has acquired the meal information (step S41: YES), the information organization unit 30 stores the meal image and the meal date and time in the first storage unit 72 (step S42). Then, the first communication unit 68 uploads the meal image and the meal date and time stored in the first storage unit 72 to the blood sugar management server 102 (step S43). Subsequently, the information organization unit 30 deletes the uploaded meal information (meal image and meal date and time) from the first storage unit 72 (step S44). Thereafter, the process proceeds to step S45.

On the other hand, when the first control unit 104 determines that the meal information acquisition unit 18 has not acquired the meal image and the meal date and time (step S41: NO), the first control unit 104 determines whether or not the blood sugar information acquisition unit 16 has acquired blood sugar information (measured value and measurement date and time) (step S45). The process of step S45 is similar to the process of step S4 described above.

When the first control unit 104 determines that the blood sugar information acquisition unit 16 has not acquired the blood sugar information (step S45: NO), the process proceeds to step S49. The process of step S49 will be described later.

On the other hand, when the first control unit 104 determines that the blood sugar information acquisition unit 16 has acquired the blood sugar information (step S45: YES), the information organization unit 30 stores the blood sugar information in the first storage unit 72 (step S46). Then, the first communication unit 68 uploads the blood sugar information stored in the first storage unit 72 to the blood sugar management server 102 (step S47). Subsequently, the information organization unit 30 deletes the uploaded blood sugar information from the first storage unit 72 (step S48).

Thereafter, the first control unit 104 determines whether or not the blood sugar management application has ended (step S49). When the blood sugar management application has ended, the current operation flow is ended. When the blood sugar management application has not ended, the process returns to step S41.

Next, the operation flow of the blood sugar management server 102 will be described.

As illustrated in FIG. 12, the server control unit 106 detects whether or not the meal image and the meal date and time have been uploaded from the blood sugar management device 100 (step S50). When the server control unit 106 detects that the upload of the meal image and the meal date and time from the blood sugar management device 100 is completed (step S50: YES), the server information organization unit 110 stores the meal image and the meal date and time in the common folder 116 (step S51). Then, the process proceeds to step S52.

On the other hand, when the meal image and the meal date and time are not uploaded from the blood sugar management device 100 (that is, a standby state) (step S50: NO), the server control unit 106 detects whether or not the blood sugar information (measured value and measurement date and time) has been uploaded from the blood sugar management device 100 (step S52). When the server control unit 106 determines that the blood sugar information has not been uploaded from the blood sugar management device 100 (step S52: NO), the current operation flow is ended (see FIG. 13).

When the server control unit 106 detects that the blood sugar information has been uploaded from the blood sugar management device 100 (step S52: YES), the server information organization unit 110 stores the blood sugar information in the common folder 116 (step S53).

Subsequently, the image determination unit 112 determines whether or not the server storage unit 114 has a meal image at a meal date and time within a predetermined time (for example, 2 hours) before a measurement date and time of the latest blood sugar information (step S54). Note that the predetermined time of step S54 is not limited to 2 hours and can be set as appropriate.

When the image determination unit 112 determines that there is no meal image (step S54: NO), the server control unit 106 requests the blood sugar management device 100 to perform notification control for prompting the subject to input meal text information (meal content memo and meal date and time) (step S55).

At this time, the notification control unit 34 of the blood sugar management device 100 outputs, for example, a voice saying "Please input meal content within 2 hours from the measurement date and time" from a speaker of the blood sugar management device 100. Further, the notification control unit 34 causes the display unit 20 of the blood sugar management device 100 to display, for example, text "Please input meal content within 2 hours from the measurement date and time". Then, when the meal text information is input to the blood sugar management device 100, the first communication unit 68 uploads the meal text information to the blood sugar management server 102.

Subsequently, the server control unit 106 determines whether or not the meal text information has been uploaded from the blood sugar management device 100 (step S56). When the server control unit 106 determines that the meal text information has not been uploaded from the blood sugar management device 100 (step S56: NO), the process remains in step S56 until the meal text information is uploaded. Note that, when it is unnecessary to collect the meal text information, the process of steps S55 to S57 can be omitted.

When the server control unit 106 determines that the meal text information has been uploaded from the blood sugar management device 100 (step S56: YES), the server information organization unit 110 stores the meal text information in the common folder 116 (step S57). Thereafter, the process proceeds to step S58 of FIG. 13.

In FIG. 12, when the image determination unit 112 determines that there is a meal image (step S54: YES), as illustrated in FIG. 13, the blood sugar determination unit 108 determines whether or not the measured value is higher than the hyperglycemia threshold value (step S58). Note that, in step S58, when the blood sugar measurement apparatus 12 is a CGM, and when the observed glucose concentration exceeds the hyperglycemia threshold value, the blood sugar determination unit 108 determines that the measured value is higher than the hyperglycemia threshold value. In this case, the blood sugar determination unit 108 may specify the highest glucose concentration in a time range exceeding the hyperglycemia threshold value and hold the highest glucose concentration as blood sugar information. This description is similarly applied to step S61 described later.

When the blood sugar determination unit 108 determines that the measured value is higher than the hyperglycemia threshold value (step S58: YES), the server information organization unit 110 copies the latest meal information (meal information corresponding to the measured value) from the common folder 116 to the hyperglycemia folder 118 and holds the latest meal information (step S59).

The server information organization unit 110 sets first deletion (step S60). Specifically, the server information organization unit 110 sets deletion of the latest meal information stored in the common folder 116. That is, the server information organization unit 110 performs setting so that, after a predetermined time (for example, 12 hours) elapses from the meal date and time of the latest meal information stored in the common folder 116, the meal information is deleted. Note that the predetermined time of step S60 is not limited to 12 hours and can be set as appropriate. Thereafter, the current operation flow is ended.

When the blood sugar determination unit 108 determines that the measured value is equal to or lower than the hyperglycemia threshold value (step S58: NO), the blood sugar determination unit 108 determines whether or not the measured value is lower than the hypoglycemia threshold value (step S61). Note that, here, when the blood sugar measurement apparatus 12 is a CGM, and when the observed glucose concentration is lower than the hypoglycemia threshold value, the blood sugar determination unit 108 determines that the measured value is lower than the hypoglycemia threshold value. When the blood sugar determination unit 108 determines that the measured value is equal to or higher than the hypoglycemia threshold value (step S61: NO), the server information organization unit 110 sets second deletion (step S62).

Specifically, the server information organization unit 110 sets deletion of the latest meal information stored in the common folder 116. That is, the server information organization unit 110 performs setting so that, after a predetermined time (for example, 12 hours) elapses from the meal date and time of the latest meal information stored in the common folder 116, the meal information is deleted. Note that the predetermined time of step S62 is not limited to 12 hours and can be set as appropriate. Thereafter, the current operation flow is ended. Note that, instead of the server information organization unit 110, the information organization unit 30 may set deletion of the latest meal information.

When the blood sugar determination unit 108 determines that the measured value is lower than the hypoglycemia threshold value (step S61: YES), the server information organization unit 110 copies meal information corresponding to the latest blood sugar information from the common folder 116 to the hypoglycemia folder 120, and holds the meal information (step S63). Specifically, the server information organization unit 110 copies meal information (for example, meal information for two meals) for a past predetermined time (for example, 12 hours) before the latest measurement date and time from the common folder 116 to the hypoglycemia folder 120 and holds the meal information. Note that the predetermined time of step S63 is not limited to 12 hours and can be set as appropriate. Then, the server information organization unit 110 deletes the latest meal information from the common folder 116 (step S64). Thereafter, the current operation flow is ended. Note that, instead of the server information organization unit 110, the information organization unit 30 may delete the latest meal information from the common folder 116.

Such a blood sugar management method includes an information acquisition step (step S41 and step S45) of acquiring blood sugar information and meal information, a storage step (step S42 and step S46) of storing the blood sugar information and the meal information acquired in the information acquisition step in the first storage unit 72, a communication step (step S43 and step S47) of uploading the blood sugar information and the meal information stored in the first storage unit 72 to the blood sugar management server 102, an information organization step (step S44) of deleting the meal information uploaded from the blood sugar management device 100 to the blood sugar management server 102 from the first storage unit 72, a server storage step (step S51 and step S53) of storing the blood sugar information and the meal information uploaded from the blood sugar management device 100 in the server storage unit 114, a blood sugar determination step (step S58 and step S61) of determining whether or not the measured value of the blood sugar information stored in the server storage unit 114 is within a predetermined range, and a server information organization step (step S59, step S60, step S62, step S63, and step S64) of organizing the meal information stored in the server storage unit 114. In the server information organization step, when it is determined in the blood sugar determination step that the measured value is within the predetermined range, meal information corresponding to the measured value is deleted from the server storage unit 114, and when it is determined in the blood sugar determination step that the measured value is not within the predetermined range, the meal information corresponding to the measured value is held in the server storage unit 114.

The blood sugar management system 10C according to the present embodiment has the following effects.

The blood sugar management system 10C includes the blood sugar management device 100 and the blood sugar management server 102. The blood sugar management device 100 includes the first storage unit 72 that stores the blood sugar information and the meal information, and the information organization unit 30 that deletes the meal information uploaded from the blood sugar management device 100 to the blood sugar management server 102 from the first storage unit 72. The blood sugar management server 102 includes the server storage unit 114 that stores the blood sugar information and the meal information uploaded from the blood sugar management device 100, the blood sugar determination unit 108 that determines whether or not the measured value is within the predetermined range, and the server information organization unit 110 that organizes the meal information stored in the server storage unit 114. When the blood sugar determination unit 108 determines that the measured value is within the predetermined range, the server information organization unit 110 deletes the meal information corresponding to the measured value from the server storage unit 114, and when the blood sugar determination unit 108 determines that the measured value is not within the predetermined range, the server information organization unit 110 holds the meal information corresponding to the measured value in the server storage unit 114.

According to such a configuration, because the meal information uploaded from the blood sugar management device 100 to the blood sugar management server 102 is deleted from the first storage unit 72, the storage capacity of the first storage unit 72 necessary for storing meal information can be reduced. Further, in the blood sugar management server 102, when the measured value is within the predetermined range, meal information corresponding to the measured value is deleted from the server storage unit 114, and thus the storage capacity of the server storage unit 114 necessary for storing meal information can be reduced. Further, when the measured value is not within the predetermined range, the meal information corresponding to the measured value is held in the server storage unit 114. In this way, only meal information considered to be particularly necessary for blood sugar management is stored in the server storage unit 114. Therefore, it is possible to efficiently find meal information related to the glucose concentration not within a predetermined range (for example, a normal range), and thus blood sugar management (treatment guidance, health guidance, etc.) can be effectively performed.

The blood sugar determination unit 108 determines whether or not the measured value is higher than the hyperglycemia threshold value, and when the blood sugar determination unit 108 determines that the measured value is higher than the hyperglycemia threshold value, the server information organization unit 110 holds the meal information corresponding to the measured value in the server storage unit 114.

According to such a configuration, meal information related to hyperglycemia can be efficiently found.

The blood sugar determination unit 108 determines whether or not the measured value is lower than the hypoglycemia threshold value, and when the blood sugar determination unit 108 determines that the measured value is lower than the hypoglycemia threshold value, the server information organization unit 110 holds the meal information corresponding to the measured value in the server storage unit 114.

According to such a configuration, meal information related to hypoglycemia can be efficiently found.

In the blood sugar management method using the blood sugar management system 10C described above, when the measured value is not within the predetermined range (lower than or equal to the hyperglycemia threshold value and higher than or equal to the hypoglycemia threshold value), the meal information of the common folder 116 is copied and held in the hyperglycemia folder 118 or the hypoglycemia folder 120. However, in the blood sugar management method, when the measured value is not within the predetermined range, the meal information corresponding to the measured value may be flagged. When the flag is set in this way, the hyperglycemia folder 118 and the hypoglycemia folder 120 become unnecessary.

The invention is not limited to the above-described embodiments, and various modifications can be implemented without departing from the gist of the invention.

The above embodiments are summarized as follows.

The embodiments disclose a blood sugar management device (14) including a blood sugar information acquisition unit (16) configured to acquire blood sugar information including a measured value, and a meal information acquisition unit (18) configured to acquire meal information including a meal image of a subject, the blood sugar management device including a storage unit (36) configured to store the blood sugar information and the meal information, a blood sugar determination unit (28) configured to determine whether or not the measured value is within a predetermined range, and an information organization unit (30) configured to organize the meal information stored in the storage unit, in which, based on determination of the blood sugar determination unit, when the blood sugar determination unit determines that the measured value is within the predetermined range, the information organization unit deletes meal information corresponding to the measured value from the storage unit, and when the blood sugar determination unit determines that the measured value is not within the predetermined range, the information organization unit holds meal information corresponding to the measured value in the storage unit.

In the blood sugar management device, the blood sugar determination unit may determine whether or not the measured value is higher than a hyperglycemia threshold value, and when the blood sugar determination unit determines that the measured value is higher than the hyperglycemia threshold value, the information organization unit may hold meal information corresponding to the measured value in the storage unit.

In the blood sugar management device, the blood sugar determination unit may determine whether or not the measured value is lower than a hypoglycemia threshold value, and when the blood sugar determination unit determines that the measured value is lower than the hypoglycemia threshold value, the information organization unit may hold meal information corresponding to the measured value in the storage unit.

In the blood sugar management device, the blood sugar management device may further include a display unit (20) configured to display the meal image held in the storage unit together with the measured value.

The blood sugar management device may further include an image determination unit (32) configured to determine whether or not the storage unit has the meal image at a meal date and time within a predetermined time before a measurement date and time of the blood sugar information, and a notification control unit (34) configured to perform notification control for prompting the subject to input text information on a meal corresponding to the measured value when the image determination unit determines that the storage unit does not have the meal image.

The embodiments disclose a blood sugar management system (10B) including a blood sugar management device (60) including a blood sugar information acquisition unit (60) configured to acquire blood sugar information including a measured value, and a meal information acquisition unit configured to acquire meal information including a meal image of a subject, and a blood sugar management server (62) configured to receive the blood sugar information and the meal information uploaded from the blood sugar management device through a network (66), in which the blood sugar management device includes a storage unit (72) configured to store the blood sugar information and the meal information, a blood sugar determination unit configured to determine whether or not the measured value is within a predetermined range, an information organization unit configured to organize the meal information stored in the storage unit, and a communication unit (68) configured to upload the meal information stored in the storage unit to the blood sugar management server, when the blood sugar determination unit determines that the measured value is not within the predetermined range, the communication unit uploads meal information corresponding to the measured value to the blood sugar management server, and when the blood sugar determination unit determines that the measured value is within the predetermined range, the information organization unit deletes meal information corresponding to the measured value from the storage unit.

In the blood sugar management system, the blood sugar determination unit may determine whether or not the measured value is higher than a hyperglycemia threshold value, and when the blood sugar determination unit determines that the measured value is higher than the hyperglycemia threshold value, the communication unit may upload meal information corresponding to the measured value to the blood sugar management server.

In the blood sugar management system, when the blood sugar determination unit determines that the measured value is higher than the hyperglycemia threshold value, after meal information corresponding to the measured value is uploaded to the blood sugar management server, the information organization unit may delete the meal information from the storage unit.

In the blood sugar management system, the blood sugar determination unit may determine whether or not the measured value is lower than a hypoglycemia threshold value, and when the blood sugar determination unit determines that the measured value is lower than the hypoglycemia threshold value, the communication unit may upload meal information corresponding to the measured value to the blood sugar management server.

In the blood sugar management system, when the blood sugar determination unit determines that the measured value is lower than the hypoglycemia threshold value, after meal information corresponding to the measured value is uploaded to the blood sugar management server, the information organization unit may delete the meal information from the storage unit.

The embodiments disclose a blood sugar management system (10C) including a blood sugar management device (100) including a blood sugar information acquisition unit configured to acquire blood sugar information including a measured value, and a meal information acquisition unit configured to acquire meal information including a meal image of a subject, and a blood sugar management server (102) configured to receive the blood sugar information and the meal information uploaded from the blood sugar management device through a network, in which the blood sugar management device includes a storage unit configured to store the blood sugar information and the meal information, and an information organization unit configured to delete the meal information uploaded from the blood sugar management device to the blood sugar management server from the storage unit, the blood sugar management server includes a server storage unit (114) configured to store the blood sugar information and the meal information uploaded from the blood sugar management device, a blood sugar determination unit (108) configured to determine whether or not the measured value is within a predetermined range, and a server information organization unit (110) configured to organize the meal information stored in the server storage unit, and when the blood sugar determination unit determines that the measured value is within the predetermined range, the server information organization unit deletes meal information corresponding to the measured value from the server storage unit, and when the blood sugar determination unit determines that the measured value is not within the predetermined range, the server information organization unit holds meal information corresponding to the measured value in the server storage unit.

In the blood sugar management system, the blood sugar determination unit may determine whether or not the measured value is higher than a hyperglycemia threshold value, and when the blood sugar determination unit determines that the measured value is higher than the hyperglycemia threshold value, the server information organization unit may hold meal information corresponding to the measured value in the server storage unit.

In the blood sugar management system, the blood sugar determination unit may determine whether or not the measured value is lower than a hypoglycemia threshold value, and when the blood sugar determination unit determines that the measured value is lower than the hypoglycemia threshold value, the server information organization unit may hold meal information corresponding to the measured value in the server storage unit.

The embodiments disclose a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a blood sugar determination step of determining whether or not the measured value is within a predetermined range, and an information organization step of organizing the meal information stored in the storage unit, in which, in the information organization step, when the measured value is within the predetermined range, meal information corresponding to the measured value is deleted from the storage unit, and when the measured value is not within the predetermined range, meal information corresponding to the measured value is held in the storage unit.

The embodiments disclose a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a blood sugar determination step of determining whether or not a measured value of the blood sugar information stored in the storage unit is within a predetermined range, a communication step of uploading meal information corresponding to the measured value to a blood sugar management server when it is determined in the blood sugar determination step that the measured value is not within the predetermined range, and an information organization step of deleting meal information corresponding to the measured value from the storage unit when it is determined in the blood sugar determination step that the measured value is within the predetermined range.

The embodiments disclose a blood sugar management method of managing blood sugar information including a measured value and meal information including a meal image of a subject, the blood sugar management method including an information acquisition step of acquiring the blood sugar information and the meal information, a storage step of storing the blood sugar information and the meal information acquired in the information acquisition step in a storage unit, a communication step of uploading the blood sugar information and the meal information stored in the storage unit to a blood sugar management server, an information organization step of deleting the meal information uploaded from a blood sugar management device to the blood sugar management server from the storage unit, a server storage step of storing the blood sugar information and the meal information uploaded from the blood sugar management device in a server storage unit, a blood sugar determination step of determining whether or not a measured value of the blood sugar information stored in the server storage unit is within a predetermined range, and a server information organization step of organizing the meal information stored in the server storage unit, in which, in the server information organization step, when it is determined in the blood sugar determination step that the measured value is within the predetermined range, meal information corresponding to the measured value is deleted from the server storage unit, and when it is determined in the blood sugar determination step that the measured value is not within the predetermined range, meal information corresponding to the measured value is held in the server storage unit.

The embodiments disclose a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a blood sugar determination step of determining whether or not the measured value is within a predetermined range, and an information organization step of organizing the meal information stored in the storage unit, in which, in the information organization step, when the measured value is within the predetermined range, meal information corresponding to the measured value is deleted from the storage unit, and when the measured value is not within the predetermined range, meal information corresponding to the measured value is held in the storage unit.

The embodiments disclose a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a blood sugar determination step of determining whether or not a measured value of the blood sugar information stored in the storage unit is within a predetermined range, a communication step of uploading meal information corresponding to the measured value to a blood sugar management server when it is determined in the blood sugar determination step that the measured value is not within the predetermined range, and an information organization step of deleting meal information corresponding to the measured value from the storage unit when it is determined in the blood sugar determination step that the measured value is within the predetermined range.

The embodiments disclose a blood sugar management program of managing blood sugar information including a measured value and meal information including a meal image of a subject, the blood sugar management program causing a computer to execute an information acquisition step of acquiring the blood sugar information and the meal information, a storage step of storing the blood sugar information and the meal information acquired in the information acquisition step in a storage unit, a communication step of uploading the blood sugar information and the meal information stored in the storage unit to a blood sugar management server, an information organization step of deleting the meal information uploaded from a blood sugar management device to the blood sugar management server from the storage unit, a server storage step of storing the blood sugar information and the meal information uploaded from the blood sugar management device in a server storage unit, a blood sugar determination step of determining whether or not a measured value of the blood sugar information stored in the server storage unit is within a predetermined range, and a server information organization step of organizing the meal information stored in the server storage unit, in which, in the server information organization step, when it is determined in the blood sugar determination step that the measured value is within the predetermined range, meal information corresponding to the measured value is deleted from the server storage unit, and when it is determined in the blood sugar determination step that the measured value is not within the predetermined range, meal information corresponding to the measured value is held in the server storage unit.

The invention claimed is:

1. A blood sugar management device comprising:
    a blood sugar information acquisition unit configured to acquire blood sugar information including a plurality of measured blood sugar values of a subject obtained over time, and a time at which each blood sugar value is obtained;
    a meal information acquisition unit configured to acquire meal information including a meal image and a time associated with the meal image;
    a storage unit comprising a common folder configured to store the blood sugar information and the meal information, a hyperglycemia folder configured to store meal information determined be associated with a blood sugar concentration higher than a hyperglycemia threshold, and a hypoglycemia folder configured to store meal information determined be associated with a blood sugar concentration lower than a hypoglycemia threshold;
    a blood sugar determination unit configured to determine whether or not one of the plurality of measured blood sugar values is within a predetermined range that is below the hyperglycemia threshold and above the hypoglycemia threshold; and
    an information organization unit configured to organize the meal information stored in the storage unit; wherein:
    when the blood sugar determination unit determines that one of the plurality of measured blood sugar values is within the predetermined range, the information organization unit deletes from the common folder meal information corresponding to the measured blood sugar value from the storage unit; and
    when the blood sugar determination unit determines that one of the plurality of measured blood sugar values is not within the predetermined range, the information organization unit associates the measured blood sugar value with the meal information, classifies the measured blood sugar value, and holds the meal information associated with the measured blood sugar value in the storage unit, wherein:
        when the blood sugar determination unit determines that the one of the plurality of measured blood sugar values is above the hyperglycemia threshold, the information organization unit copies the corresponding meal information from the common folder to the hyperglycemia folder and sets the corresponding meal information for deletion from the common folder, and
        when the blood sugar determination unit determines that the one of the plurality of measured blood sugar values is below the hypoglycemia threshold, the information organization unit copies the corresponding meal information from the common folder to the hypoglycemia folder and sets the corresponding meal information for deletion from the common folder.

2. The blood sugar management device according to claim 1, further comprising:
    a display unit configured to display the meal image held in the storage unit together with the measured blood sugar value.

3. The blood sugar management device according to claim 1, further comprising:
    an image determination unit configured to determine whether or not the storage unit has the meal image at a meal date and time within a predetermined time before a measurement date and time of the blood sugar information; and
    a notification control unit configured to prompt the subject to input text information on a meal corresponding to the measured blood sugar value when the image determination unit determines that the storage unit does not have the meal image.

4. A blood sugar management system comprising:
    a blood sugar management device comprising:
        a blood sugar information acquisition unit configured to acquire blood sugar information including a plurality of measured blood sugar values of a subject obtained over time, and a time at which each blood sugar value is obtained,
        a meal information acquisition unit configured to acquire meal information including a meal image and a time associated with the meal image, a management device storage unit configured to store the blood sugar information and the meal information, a blood sugar determination unit configured to determine whether or not one of the plurality of measured blood sugar value is within a predetermined range that is below a hyperglycemia threshold and above a hypoglycemia threshold, an information organization unit configured to organize the meal information stored in the storage unit, an image determination unit configured to determine whether or not the storage unit has the meal image at a time of a meal within a predetermined time before a measurement time of the blood sugar information, and a notification control unit configured to prompt the subject to input text information on a meal corresponding to the measured blood sugar value when the image determination unit determines that the storage unit does not have the meal image; and a communication unit configured to upload the meal information stored in the management device storage unit through a network; and a blood sugar management server configured to receive the blood sugar information and the meal information uploaded from the blood sugar management device; wherein:

when the blood sugar determination unit determines that one of the plurality of measured blood sugar values is within the predetermined range, the information organization unit deletes meal information corresponding to the measured blood sugar value from the management device storage unit, and when the blood sugar determination unit determines that one of the plurality of measured blood sugar values is not within the predetermined range, the information organization unit associates the measured blood sugar value with the meal information, and the communication unit uploads meal information associated with the measured blood sugar value to the blood sugar management server; wherein:

when the blood sugar determination unit determines that the measured blood sugar value is higher than the hyperglycemia threshold value, the communication unit uploads meal information corresponding to the measured blood sugar value to the blood sugar management server, and after meal information corresponding to the measured blood sugar value is uploaded to the blood sugar management server, the information organization unit deletes the meal information from the management device storage unit and deletes the meal information from the storage unit, and when the blood sugar determination unit determines that the measured blood sugar value is lower than the hypoglycemia threshold value, the communication unit uploads meal information corresponding to the measured blood sugar value to the blood sugar management server and, after meal information corresponding to the measured blood sugar value is uploaded to the blood sugar management server, the information organization unit deletes the meal information from the storage unit.

5. A blood sugar management system comprising:

a blood sugar management device comprising:

a blood sugar information acquisition unit configured to acquire blood sugar information including a plurality of measured blood sugar values of a subject obtained over time, and a time at which each blood sugar value is obtained, a meal information acquisition unit configured to acquire meal information including a meal image and a time associated with the meal image, a management device storage unit configured to store the blood sugar information and the meal information, and an information organization unit configured to delete the meal information uploaded from the blood sugar management device to the blood sugar management server from the storage unit;

a blood sugar management server configured to receive the blood sugar information and meal information uploaded from the blood sugar management device through a network, the blood sugar management server comprising:

a server storage unit comprising a common folder configured to store the blood sugar information and the meal information uploaded from the blood sugar management device, a hyperglycemia folder configured to store meal information determined be associated with a blood sugar concentration higher than a hyperglycemia threshold, and a hypoglycemia folder configured to store meal information determined be associated with a blood sugar concentration lower than a hypoglycemia threshold, a blood sugar determination unit configured to determine whether or not one of the plurality of measured blood sugar value is within a predetermined range that is below the hyperglycemia threshold and above the hypoglycemia threshold, and a server information organization unit configured to organize the meal information stored in the server storage unit; wherein when the blood sugar determination unit determines that one of the plurality of measured blood sugar values is within the predetermined range, the server information organization unit deletes meal information corresponding to the measured blood sugar value from the common folder of the server storage unit; and when the blood sugar determination unit determines that one of the plurality of measured blood sugar values is not within the predetermined range, the server information organization unit associates the measured blood sugar value with the meal information, classifies the measured blood sugar value, and holds meal information corresponding to the measured blood sugar value in the server storage unit, wherein:

when the blood sugar determination unit determines that the one of the plurality of measured blood sugar values is above the hyperglycemia threshold, the server information organization unit copies the corresponding meal information from the common folder to the hyperglycemia folder and sets the corresponding meal information for deletion from the common folder, and when the blood sugar determination unit determines that the one of the plurality of measured blood sugar values is below the hypoglycemia threshold, the server information organization unit copies the corresponding meal information from the common folder to the hypoglycemia folder and sets the corresponding meal information for deletion from the common folder.

6. The blood sugar management device according to claim 1, wherein the blood sugar determination unit is configured to acquire the blood sugar information from a continuous glucose monitor.

7. The blood sugar management device according to claim 1, further comprising:
- a graph creation unit configured to create a graph of the measured blood sugar values over time;
- a display unit configured to display the graph of the measured blood sugar values over time along with meal images copied from the common folder to either the hyperglycemia folder or the hypoglycemia folder.

8. The blood sugar management device according to claim 7, wherein the meal images are displayed on the graph if the measured blood sugar values do not fall below the hypoglycemia threshold value within a predetermined time.

9. The blood sugar management system according to claim 4, wherein the blood sugar determination unit is configured to acquire the blood sugar information from a continuous glucose monitor.

10. The blood sugar management system according to claim 4, wherein:
- the blood sugar management device further comprises:
  - a graph creation unit configured to create a graph of the measured blood sugar values over time, and
  - a display unit configured to display the graph of the measured blood sugar values over time along with meal images copied from the management device storage unit.

11. The blood sugar management system according to claim 10, wherein the meal images are displayed on the graph if the measured blood sugar values do not fall below the hypoglycemia threshold value within a predetermined time.

12. The blood sugar management system according to claim 5, wherein the blood sugar determination unit is configured to acquire the blood sugar information from a continuous glucose monitor.

13. The blood sugar management system according to claim 5, wherein:
- the blood sugar management device further comprises:
  - a graph creation unit configured to create a graph of the measured blood sugar values over time,
  - a display unit configured to display the graph of the measured blood sugar values over time along with meal images copied from the common folder to either the hyperglycemia folder or the hypoglycemia folder.

14. The blood sugar management system according to claim 13, wherein the meal images are displayed on the graph if the measured blood sugar values do not fall below the hypoglycemia threshold value within a predetermined time.

* * * * *